(12) United States Patent
Witowski et al.

(10) Patent No.: US 9,364,476 B2
(45) Date of Patent: Jun. 14, 2016

(54) METHODS OF TREATING A BRUTON'S TYROSINE KINASE DISEASE OR DISORDER

(71) Applicant: Celgene Avilomics Research, Inc., Bedford, MA (US)

(72) Inventors: Steven Richard Witowski, Melrose, MA (US); William Frederick Westlin, III, Boxborough, MA (US); Heather Lounsbury, Framingham, MA (US); Kathryn Stiede, Hollis, NH (US); Bruce A. Silver, Dunkirk, MD (US); Jay M. Mei, North Wales, PA (US)

(73) Assignee: Celgene Avilomics Research, Inc., Cambridge, MA (US)

( * ) Notice: Subject to any disclaimer, the term of this patent is extended or adjusted under 35 U.S.C. 154(b) by 261 days.

(21) Appl. No.: 13/661,678

(22) Filed: Oct. 26, 2012

(65) Prior Publication Data

US 2013/0109709 A1    May 2, 2013

Related U.S. Application Data

(60) Provisional application No. 61/552,936, filed on Oct. 28, 2011, provisional application No. 61/569,475, filed on Dec. 12, 2011, provisional application No. 61/592,351, filed on Jan. 30, 2012, provisional application No. 61/593,056, filed on Jan. 31, 2012, provisional application No. 61/604,780, filed on Feb. 29, 2012, provisional application No. 61/618,347, filed on Mar. 30, 2012, provisional application No. 61/649,450, filed on May 21, 2012, provisional application No. 61/660,319, filed on Jun. 15, 2012.

(51) Int. Cl.
*A61K 31/505* (2006.01)
*A61K 31/506* (2006.01)
*A61K 9/48* (2006.01)

(52) U.S. Cl.
CPC ............. *A61K 31/505* (2013.01); *A61K 9/4866* (2013.01); *A61K 31/506* (2013.01)

(58) Field of Classification Search
None
See application file for complete search history.

(56) References Cited

U.S. PATENT DOCUMENTS

| | | | |
|---|---|---|---|
| 4,879,303 A | 11/1989 | Davison et al. |
| 5,958,935 A | 9/1999 | Davis et al. |
| 6,093,716 A | 7/2000 | Davis et al. |
| 6,114,333 A | 9/2000 | Davis et al. |
| 6,127,376 A | 10/2000 | Davey et al. |
| 6,160,010 A | 12/2000 | Uckun et al. |
| 6,262,088 B1 | 7/2001 | Phillips |
| 6,469,168 B1 | 10/2002 | Ratzne Simonek et al. |
| 6,579,983 B1 | 6/2003 | Batchelor et al. |
| 6,593,326 B1 | 7/2003 | Bradbury et al. |
| 6,838,464 B2 | 1/2005 | Pease et al. |
| 6,939,874 B2 | 9/2005 | Harmange et al. |
| 7,060,827 B2 | 6/2006 | Singh et al. |
| 7,122,542 B2 | 10/2006 | Singh et al. |
| 7,125,879 B2 | 10/2006 | Guillemont et al. |
| 7,176,212 B2 | 2/2007 | Breault et al. |
| 7,202,033 B2 | 4/2007 | Prescott et al. |
| 7,241,769 B2 | 7/2007 | Stadtmueller et al. |
| 7,282,504 B2 | 10/2007 | Armistead et al. |
| 7,329,671 B2 | 2/2008 | Singh et al. |
| 7,329,672 B2 | 2/2008 | Singh et al. |
| 7,332,484 B2 | 2/2008 | Singh et al. |
| 7,435,814 B2 | 10/2008 | Singh et al. |
| 7,452,879 B2 | 11/2008 | Singh et al. |
| 7,485,724 B2 | 2/2009 | Singh et al. |
| 7,491,732 B2 | 2/2009 | Li et al. |
| 7,498,435 B2 | 3/2009 | Singh et al. |
| 7,504,396 B2 | 3/2009 | Nunes et al. |
| 7,514,444 B2 | 4/2009 | Honigberg et al. |
| 7,514,445 B2 | 4/2009 | Freyne et al. |
| 7,514,446 B2 | 4/2009 | Davis-Ward et al. |
| 7,517,886 B2 | 4/2009 | Singh et al. |
| 7,528,143 B2 | 5/2009 | Noronha et al. |
| 7,531,548 B2 | 5/2009 | Guillemont et al. |
| 7,550,460 B2 | 6/2009 | Singh et al. |
| 7,557,210 B2 | 7/2009 | Singh et al. |
| 7,582,648 B2 | 9/2009 | Singh et al. |
| 7,589,200 B2 | 9/2009 | Singh et al. |
| 7,642,351 B2 | 1/2010 | Singh et al. |
| 7,655,797 B2 | 2/2010 | Singh et al. |
| 7,718,662 B1 | 5/2010 | Chen et al. |
| 7,741,330 B1 | 6/2010 | Chen et al. |
| 7,803,939 B2 | 9/2010 | Singh et al. |
| 7,812,029 B1 | 10/2010 | Singh et al. |

(Continued)

FOREIGN PATENT DOCUMENTS

| CN | 102558149 A | 7/2012 |
|---|---|---|
| CN | 103159742 A | 6/2013 |

(Continued)

OTHER PUBLICATIONS

Merriam-Webster's Online Dictionary, "Prevent", downloaded on Apr. 7, 2008 from "http://www.merriam-webster.com/dictionary/prevent", p. 1 of 1.*
U.S. Appl. No. 13/518,833, filed Jun. 22, 2012, Gray et al.
U.S. Appl. No. 14/058,847, filed Oct. 21, 2013, Celgene Avilomics Research, Inc.
U.S. Appl. No. 14/448,578, filed Jul. 31, 2014, Kwangho Lee, et al.
[Author Not Known], A predictive model for aggressive non-Hodgkin lymphoma. The International Non-Hodgkin's Lymphoma Prognostic Factors Project, New England Journal of Medicine, 329:987-994 (1993).

(Continued)

*Primary Examiner* — Savitha Rao
*Assistant Examiner* — Gregg Polansky
(74) *Attorney, Agent, or Firm* — Choate, Hall, & Stewart LLP; Charles E. Lyon; Kristen C. Buteau

(57) ABSTRACT

The present invention provides methods of treating, stabilizing or lessening the severity or progression of a disease or disorder associated with BTK.

26 Claims, 8 Drawing Sheets

(56) References Cited

U.S. PATENT DOCUMENTS

| | | | |
|---|---|---|---|
| 7,820,819 B2 | 10/2010 | Singh et al. |
| 7,825,116 B2 | 11/2010 | Singh et al. |
| 7,858,633 B2 | 12/2010 | Li et al. |
| 7,884,111 B2 | 2/2011 | Argade et al. |
| 7,906,644 B2 | 3/2011 | Singh et al. |
| 8,088,781 B2 | 1/2012 | Honigberg et al. |
| 8,148,525 B2 | 4/2012 | Singh et al. |
| 8,158,621 B2 | 4/2012 | Singh et al. |
| 8,188,276 B2 | 5/2012 | Singh et al. |
| 8,334,296 B2 | 12/2012 | Singh et al. |
| 8,338,439 B2 | 12/2012 | Singh et al. |
| 8,450,335 B2 | 5/2013 | Singh et al. |
| 8,501,751 B2 | 8/2013 | Honigberg et al. |
| 8,557,806 B2 | 10/2013 | Singh et al. |
| 8,563,568 B2 | 10/2013 | Witowski et al. |
| 8,609,679 B2 | 12/2013 | Singh et al. |
| 8,710,222 B2 | 4/2014 | Singh et al. |
| 8,735,404 B2 | 5/2014 | Honigberg et al. |
| 8,748,438 B2 | 6/2014 | Honigberg et al. |
| 8,748,597 B2 | 6/2014 | Singh et al. |
| 8,796,255 B2 | 8/2014 | Lee et al. |
| 8,822,685 B2 | 9/2014 | Singh et al. |
| 8,835,430 B2 | 9/2014 | Singh et al. |
| 8,853,397 B2 | 10/2014 | Singh et al. |
| 8,883,435 B2 | 11/2014 | Honigberg et al. |
| 8,883,803 B2 | 11/2014 | Honigberg et al. |
| 8,975,249 B2 | 3/2015 | Lee et al. |
| 2004/0019067 A1 | 1/2004 | Armistead et al. |
| 2004/0023957 A1 | 2/2004 | Wang et al. |
| 2004/0077661 A1 | 4/2004 | Arbiser |
| 2005/0004125 A1 | 1/2005 | Freyne et al. |
| 2005/0014753 A1 | 1/2005 | Ding et al. |
| 2005/0085637 A1 | 4/2005 | Cheung et al. |
| 2005/0209221 A1 | 9/2005 | Nunes et al. |
| 2005/0272083 A1 | 12/2005 | Seshagiri |
| 2006/0030018 A1 | 2/2006 | Zuccola et al. |
| 2006/0079543 A1 | 4/2006 | Sum et al. |
| 2006/0084644 A1 | 4/2006 | Pal et al. |
| 2006/0084645 A1 | 4/2006 | Pal et al. |
| 2006/0100227 A1 | 5/2006 | Baenteli et al. |
| 2006/0148800 A1 | 7/2006 | Stadtmueller et al. |
| 2006/0160803 A1 | 7/2006 | Adams et al. |
| 2006/0247241 A1 | 11/2006 | Garcia-Echeverria et al. |
| 2006/0247262 A1 | 11/2006 | Baenteli et al. |
| 2006/0270694 A1 | 11/2006 | Wong |
| 2006/0293311 A1 | 12/2006 | Li et al. |
| 2007/0010668 A1 | 1/2007 | Davis-Ward et al. |
| 2007/0032493 A1 | 2/2007 | Foley et al. |
| 2007/0066658 A1 | 3/2007 | Chappell |
| 2007/0141143 A1* | 6/2007 | Smithey et al. |
| 2007/0203161 A1 | 8/2007 | Argade et al. |
| 2007/0203162 A1 | 8/2007 | Li et al. |
| 2007/0208034 A1* | 9/2007 | Stadlwieser |
| 2007/0259904 A1 | 11/2007 | Noronha et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0039622 A1 | 2/2008 | Singh et al. |
| 2008/0058358 A1 | 3/2008 | Luecking et al. |
| 2008/0076921 A1 | 3/2008 | Honigberg et al. |
| 2008/0132504 A1 | 6/2008 | Garcia-Echeverria et al. |
| 2008/0139582 A1 | 6/2008 | Honigberg et al. |
| 2008/0182852 A1 | 7/2008 | Johnson et al. |
| 2008/0194603 A1 | 8/2008 | Li et al. |
| 2008/0207613 A1 | 8/2008 | Styles et al. |
| 2008/0214501 A1 | 9/2008 | Pan et al. |
| 2008/0260754 A1 | 10/2008 | Li et al. |
| 2008/0279867 A1 | 11/2008 | Atuegbu et al. |
| 2008/0300268 A1 | 12/2008 | Singh et al. |
| 2008/0312438 A1 | 12/2008 | Singh et al. |
| 2009/0131436 A1 | 5/2009 | Imbach et al. |
| 2009/0137588 A1 | 5/2009 | Singh et al. |
| 2009/0156622 A1 | 6/2009 | Singh et al. |
| 2009/0171086 A1 | 7/2009 | Singh et al. |
| 2009/0181987 A1 | 7/2009 | Honigberg et al. |
| 2009/0215803 A1 | 8/2009 | Rice et al. |
| 2009/0286778 A1 | 11/2009 | Combs et al. |
| 2009/0298830 A1 | 12/2009 | Mann et al. |
| 2009/0318407 A1 | 12/2009 | Bauer et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0029610 A1* | 2/2010 | Singh et al. |
| 2010/0041677 A1 | 2/2010 | Honigberg et al. |
| 2010/0081679 A1 | 4/2010 | Greul et al. |
| 2010/0088912 A1 | 4/2010 | Higgs et al. |
| 2010/0173285 A1 | 7/2010 | Varmus et al. |
| 2010/0197918 A1 | 8/2010 | Singh et al. |
| 2010/0254905 A1 | 10/2010 | Honigberg et al. |
| 2011/0039868 A1 | 2/2011 | Honigberg et al. |
| 2011/0105472 A1 | 5/2011 | Greul et al. |
| 2011/0144330 A1 | 6/2011 | Singh et al. |
| 2011/0207736 A1 | 8/2011 | Gray et al. |
| 2011/0224235 A1 | 9/2011 | Honigberg et al. |
| 2011/0245156 A1 | 10/2011 | Sielecki-Dzurdz |
| 2011/0245284 A1 | 10/2011 | Greul et al. |
| 2011/0281322 A1 | 11/2011 | Honigberg et al. |
| 2011/0281850 A1 | 11/2011 | Flynn et al. |
| 2012/0040968 A1 | 2/2012 | Shimada et al. |
| 2012/0065201 A1 | 3/2012 | Honigberg et al. |
| 2012/0071497 A1 | 3/2012 | Buggy et al. |
| 2012/0083006 A1 | 4/2012 | Ramsden et al. |
| 2012/0087915 A1 | 4/2012 | Buggy et al. |
| 2012/0088912 A1 | 4/2012 | Honigberg et al. |
| 2012/0094999 A1 | 4/2012 | Gray et al. |
| 2012/0101113 A1 | 4/2012 | Honigberg et al. |
| 2012/0101114 A1 | 4/2012 | Honigberg et al. |
| 2012/0149687 A1 | 6/2012 | Lee et al. |
| 2012/0149722 A1 | 6/2012 | Lee et al. |
| 2012/0165328 A1 | 6/2012 | Honigberg et al. |
| 2012/0165332 A1 | 6/2012 | Major et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0270237 A9 | 10/2012 | Ramsden et al. |
| 2012/0296089 A1 | 11/2012 | Honigberg et al. |
| 2012/0316135 A1 | 12/2012 | Dalgarno et al. |
| 2012/0329130 A1 | 12/2012 | Honigberg et al. |
| 2013/0035334 A1 | 2/2013 | Honigberg et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0137708 A1 | 5/2013 | Garske et al. |
| 2013/0165462 A1 | 6/2013 | Singh et al. |
| 2014/0057929 A1 | 2/2014 | Witowski et al. |
| 2014/0134265 A1 | 5/2014 | Buggy et al. |
| 2014/0142123 A1 | 5/2014 | Honigberg et al. |
| 2014/0163027 A1 | 6/2014 | Verner et al. |
| 2014/0163046 A1 | 6/2014 | Honigberg et al. |
| 2014/0187564 A1 | 7/2014 | Honigberg et al. |
| 2014/0187565 A1 | 7/2014 | Honigberg et al. |
| 2014/0213574 A1 | 7/2014 | Singh et al. |
| 2014/0303154 A1 | 10/2014 | Singh et al. |
| 2014/0303191 A1 | 10/2014 | Buggy et al. |
| 2014/0330007 A1 | 11/2014 | Singh et al. |
| 2014/0371241 A1 | 12/2014 | Buggy et al. |
| 2015/0005297 A1 | 1/2015 | Singh et al. |
| 2015/0025055 A1 | 1/2015 | Lee et al. |
| 2015/0038518 A1 | 2/2015 | Balasubramanian |
| 2015/0126504 A1 | 5/2015 | Singh et al. |
| 2015/0158823 A1 | 6/2015 | Singh et al. |
| 2015/0246040 A1 | 9/2015 | Lee et al. |

FOREIGN PATENT DOCUMENTS

| | | |
|---|---|---|
| EP | 1 054 004 A1 | 11/2000 |
| JP | 07041461 A | 2/1995 |
| WO | WO-96/28427 A1 | 9/1996 |
| WO | WO-97/19065 A1 | 5/1997 |
| WO | WO-00/27825 A1 | 5/2000 |
| WO | WO-00/46203 A2 | 8/2000 |
| WO | WO-00/78731 A1 | 12/2000 |
| WO | WO-01/47897 A1 | 7/2001 |

(56) References Cited

FOREIGN PATENT DOCUMENTS

| WO | WO-01/60816 A1 | 8/2001 |
|---|---|---|
| WO | WO-01/64654 A1 | 9/2001 |
| WO | WO-01/64655 A1 | 9/2001 |
| WO | WO-01/85699 A2 | 11/2001 |
| WO | WO-02/083653 A1 | 10/2002 |
| WO | WO-03/016306 A1 | 2/2003 |
| WO | WO-03/030909 A1 | 4/2003 |
| WO | WO-03/063794 A2 | 8/2003 |
| WO | WO-03/066601 A1 | 8/2003 |
| WO | WO-2004/014382 A1 | 2/2004 |
| WO | WO-2004/031232 A1 | 4/2004 |
| WO | WO-2004/056786 A2 | 7/2004 |
| WO | WO-2004/069812 A1 | 8/2004 |
| WO | WO-2004/074244 A2 | 9/2004 |
| WO | WO-2004/080980 A1 | 9/2004 |
| WO | WO-2004/096224 A2 | 11/2004 |
| WO | WO-2005/013996 A1 | 2/2005 |
| WO | WO-2005/016893 A2 | 2/2005 |
| WO | WO-2005/016894 A1 | 2/2005 |
| WO | WO-2005/026130 A1 | 3/2005 |
| WO | WO-2005/026158 A1 | 3/2005 |
| WO | WO-2005/063722 A1 | 7/2005 |
| WO | WO-2005/070890 A2 | 8/2005 |
| WO | WO-2006/021544 A1 | 3/2006 |
| WO | WO-2006/045066 A2 | 4/2006 |
| WO | WO-2006/053109 A1 | 5/2006 |
| WO | WO-2006/055561 A2 | 5/2006 |
| WO | WO-2006/068770 A1 | 6/2006 |
| WO | WO-2006/074057 A2 | 7/2006 |
| WO | WO-2006/078846 A1 | 7/2006 |
| WO | WO-2006/101977 A2 | 9/2006 |
| WO | WO-2006/108487 A1 | 10/2006 |
| WO | WO-2006/124874 A2 | 11/2006 |
| WO | WO-2006/128129 A2 | 11/2006 |
| WO | WO-2006/129100 A1 | 12/2006 |
| WO | WO-2006/133426 A2 | 12/2006 |
| WO | WO-2007/027238 A2 | 3/2007 |
| WO | WO-2007/048064 A2 | 4/2007 |
| WO | WO-2007/053452 A1 | 5/2007 |
| WO | WO-2007/056151 A2 | 5/2007 |
| WO | WO-2007/085833 A2 | 8/2007 |
| WO | WO-2007/089768 A2 | 8/2007 |
| WO | WO-2007/113254 A1 | 10/2007 |
| WO | WO-2007/113256 A1 | 10/2007 |
| WO | WO-2007/120339 A1 | 10/2007 |
| WO | WO-2007/120980 A2 | 10/2007 |
| WO | WO-2007/125351 A1 | 11/2007 |
| WO | WO-2008/005538 A2 | 1/2008 |
| WO | WO-2008/009458 A1 | 1/2008 |
| WO | WO-2008/025556 A1 | 3/2008 |
| WO | WO-2008/049123 A2 | 4/2008 |
| WO | WO-2008/064274 A1 | 5/2008 |
| WO | WO-2008/073687 A2 | 6/2008 |
| WO | WO-2008/074515 A1 | 6/2008 |
| WO | WO-2008/079719 A1 | 7/2008 |
| WO | WO-2008/079907 A1 | 7/2008 |
| WO | WO-2008/080964 A1 | 7/2008 |
| WO | WO-2008/080965 A2 | 7/2008 |
| WO | WO-2008/088303 A1 | 7/2008 |
| WO | WO-2008/092199 A1 | 8/2008 |
| WO | WO-2008/107096 A1 | 9/2008 |
| WO | WO-2008/115738 A1 | 9/2008 |
| WO | WO-2008/115742 A1 | 9/2008 |
| WO | WO-2008/118822 A1 | 10/2008 |
| WO | WO-2008/118823 A2 | 10/2008 |
| WO | WO-2009/012421 A1 | 1/2009 |
| WO | WO-2009/017838 A2 | 2/2009 |
| WO | WO-2009/029682 A1 | 3/2009 |
| WO | WO-2009/032668 A2 | 3/2009 |
| WO | WO-2009/032694 A1 | 3/2009 |
| WO | WO-2009/032703 A1 | 3/2009 |
| WO | WO-2009/080638 A2 | 7/2009 |
| WO | WO-2009/105675 A1 | 8/2009 |
| WO | WO-2009/112490 A1 | 9/2009 |
| WO | WO-2009/115267 A2 | 9/2009 |
| WO | WO-2009/127642 A2 | 10/2009 |
| WO | WO-2009/132202 A2 | 10/2009 |
| WO | WO-2009/136995 A2 | 11/2009 |
| WO | WO-2009/143389 A1 | 11/2009 |
| WO | WO-2009/158571 A1 | 12/2009 |
| WO | WO-2010/025833 A1 | 3/2010 |
| WO | WO-2010/081679 A2 | 7/2010 |
| WO | WO-2010/129053 A2 | 11/2010 |
| WO | WO-2011/079231 A1 | 6/2011 |
| WO | WO-2011/090760 A1 | 7/2011 |
| WO | WO-2011/140338 A1 | 11/2011 |
| WO | WO-2011/153514 A2 | 12/2011 |
| WO | WO-2012/021444 A1 | 2/2012 |
| WO | WO-2012/061299 A1 | 5/2012 |
| WO | WO-2012/061303 A1 | 5/2012 |
| WO | WO-2012/061415 A1 | 5/2012 |
| WO | WO-2012/064706 A1 | 5/2012 |
| WO | WO-2012/158843 A2 | 11/2012 |
| WO | WO-2013/063401 A1 | 5/2013 |

OTHER PUBLICATIONS

[Author Not Known], Guidance for Industry, Estimating the maximum safe starting dose in initial clinical trials for therapeutics in adult healthy volunteers, U.S. Department of Health and Human Services, Food and Drug Administration, Center for Drug Evaluation and Research (CDER), Pharmacology and Toxicology, retrieved on Jul. 2005 http://www.fda.gov/downloads/Drugs/GuidanceCompliance/Regulatory/Information/Gui.

[Author Not Known], What are the key statistics about Waldenstrom Macroglobulinemia?, (accessed Dec. 16, 2014) http://www.cancer.org/cancer/waldenstrommacroglobulinemia/detailedguide/waldenstrom-macroglobulinemia-key-statistics-w-m.

Aliagas-Martin, I. et al., A class of 2,4-bisanilinopyrimidine Aurora A inhibitors with unusually high selectivity against Aurora B, J. Med. Chem. 52:3300-3307 (2009).

Andrulis, I. et al., Neu/ErbB-2 amplification identifies a poor-prognosis group of women with node-negative breast cancer, J Clin Oncol 16:1340-9 (1998).

Baba, Y. et al., BLNK mediates Syk-dependent Btk activation, Proceedings of the National Academy of Sciences of the USA, 98(5):2582-2586 (2001).

Bamborough P. et al., N-4-Pyrimidinyl-1H-indazol-4-amine inhibitors of Lck: Indazoles as phenol isosteres with improved pharmacokinetics, Bioorg. & Med. Chem. Lett. 17:4363-4368 (2007).

Binet, J. et al., A new prognostic classification of chronic lymphocytic leukemia derived from a multivariate survival analysis, Cancer, 48:198-206 (1981).

Braselmann, S. et al., R406, an orally available spleen tyrosine kinase inhibitor blocks Fc receptor signaling and reduces immune complex-mediated inflammation, Journal of Pharmacology Experimental Therapeutics, 319(3):998-1008, 2006.

Burger, J. et al., The Bruton's tyrosine kinase inhibitor, PCI-32765, is well tolerated and demonstrates promising clinical activity in chronic lymphocytic leukemia (CLL) and small lymphocytic lymphoma (SLL): an update on ongoing phase 1 studies, Blood, 116(21): Abstract 57 (2010).

Calvo, E. et al., Administration of CI-1033, an Irreversible Pan-erbB Tyrosine Kinase Inhibitor, Is Feasible on a 7-Day Off Schedule: A Phase I Pharmacokinetic and Food Effect Study, Clinical Cancer Research, 10: 7112-7120 (2004).

Campana, D. et al., Phenotypic features and proliferative activity of B cell progenitors in X-linked agammaglobulinemia, The Journal of Immunology, 145(6):1675-1680 (1990).

Carter, T. et al, Inhibition of drug-resistant mutants of ABL, KIT, and EGF receptor kinases, Proc. Natl. Acad. Sci. USA 102(31):11011-11016 (2005).

Cheson, B. et al., Revised response criteria for malignant lymphoma, Journal of Clinical Oncology, 25(5):579-586 (2007).

Cohen, M. et al., Structural bioinformatics-based design of selective, irreversible inhibitors, Science 308:1318-1321 (2005).

Coiffier, B. et al., Long-term results of the GELA study comparing R-CHOP and CHOP chemotherapy in older patients with diffuse

(56) References Cited

OTHER PUBLICATIONS large B cell lymphoma show good survival in poor risk patients, Journal of Clinical Oncology, 25(18) Suppl., pt.1., Abstract 8009 (2007).
Conley, M. et al., Primary B Cell Immunodeficiencies: Comparisons and Contrasts, Annual Review of Immunology, 27:199-227 (2009).
Curto, M. et al., Contact-dependent inhibition of EGFR signaling by Nf2/Merlin, J Cell Biol 177:893-903 (2007).
Damle, R. et al., Ig V Gene Mutation Status and CD38 Expression As Novel Prognostic Indicators in Chronic Lymphocytic Leukemia, Blood, 94(6):1840-1847 (1999).
Dave, S. et al., Prediction of survival in follicular lymphoma based on molecular features of tumor-infiltrating immune cells, New England Journal of Medicine, 351(21):2159-2169 (2004).
Davis, R. et al., Chronic active B-cell-receptor signaling in diffuse large B-cell lymphoma, Nature, 463:88-92 (2010).
Dimopoulos, M. et al., Update on treatment recommendations from the Fourth International Workshop on Waldenström's Macroglobulinemia, Journal of Clinical Oncology, 27(1):120-126 (2009).
Dimopoulos, M. et al., Waldenström's Macroglobulinemia, Hematology/Oncology Clinics of North America, 13(6):1351-1366 (1999).
Ding, K. et al., Design, Synthesis and Biological Evaluation of Novel Conformationally Constrained Inhibitors Targeting Epidermal Growth Factor Receptor T790M mutant, J. Med. Chem. Feb. 16, 2012, DOI: 10.1021/jm201591k.
Dohner, H. et al., Genomic aberrations and survival in chronic lymphocytic leukemia, New England Journal of Medicine, 343:1910-1916 (2000).
Elder, D.P. et al., The utility of sulfonate salts in drug development, J Pharm Sci., 99(7):2948-61 (2010).
Extended European Search Report for EP11816874.9, 5 pages (Dec. 12, 2013).
Extended European Search Report for EP11838624.2, 5 pages (Jun. 6, 2014).
Extended European Search Report for EP11838628.3, 7 pages (Jun. 20, 2014).
Extended European Search Report for EP11839800.7, 8 pages (Jun. 24, 2014).
Fabian, M. et al., A small molecule-kinase interaction map for clinical kinase inhibitors, Nature Biotechnology, 23(3): 329 (2005).
Fallon, K. et al., Constitutive activation of the neuregulin-1/erbB signaling pathway promotes the proliferation of a human peripheral neuroepithelioma cell line, J Neuro Oncol 66:273-84 (2004).
Fisher, R. et al., Comparison of a standard regimen (CHOP) with three intensive chemotherapy regimens for advanced non-Hodgkin's lymphoma, New England Journal of Medicine, 328:1002-1006 (1993).
Fisher, R. et al., Diffuse aggressive lymphoma, Hematology (American Society of Hematology), 221-236 (2004).
Fowler, N. et al., The Btk inhibitor, PCI-32765, induces durable responses with minimal toxicity in patients with relapsed/refractory B cell malignancies: Results from a phase I study, Blood, 116(21): Abstract 964 (2010).
Frank, D., STAT signaling in the pathogenesis and treatment of cancer, Mol. Med. 5 :432-456 (1999).
Friedberg, J. et al., Inhibition of Syk with fostamatinib disodium has significant clinical activity in non-Hodgkin lymphoma and chronic lymphocytic leukemia, Blood, 115(13):2578-2585 (2010).
Fry, D. et al., Specific, irreversible inactivation of the epidermal growth factor receptor and erbB2, by a new class of tyrosine kinase inhibitor, Proc. Natl. Acad. Sci. USA 95:12022-12027 (1998).
Furman, R. et al., CAL-101, an isoform-selective inhibitor of phosphatidylinositol 3-kinase P1008, demonstrates clinical activity and pharmacodynamic effects in patients with relapsed or refractory chronic lymphocytic leukemia, Blood, 116(21): Abstract 55 (2010).
Furman, Richard R., Prognostic markers and stratification of chronic lymphocytic leukemia, Hematology (American Society of Hematology), pp. 77-81 (2010).
Gauld, S. et al., B cell antigen receptor signaling: roles in cell development and disease, Science, 296:1641-1642 (2002).
Ghoneim, K., Synthesis and evaluation of some 2-, 4-, di- substituted -6-methylpyrimidine derivatives for antimicrobial activity, J. Indian Chem. Soc. 63(10):914-917 (1986).
Ghosh, D., 2-4-bis (arylamino)-5-methylpyrimidines as antimicrobial agents, J. Med. Chem. 10(5):974 (1967).
Ghosh, D., 2-4-bis (arylamino)-6-methylpyrimidines as antimicrobial agents, J. Indian Chem. Soc. 58(5):512-573 (1981).
Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (2008).
Gordon, A. et al., The kinase inhibitor, PCI-32765, demonstrates activity in chronic lymphocytic leukemia cell independent of microenvironmental survival signals, Blood 116(21): Abstract 1385 (2010).
Guarini, A. et al., BCR ligation induced by IgM stimulation results in gene expression and functional changes only in IgVH unmutated chronic lymphocytic leukemia (CLL) cells, Blood, 112:782-792 (2008).
Gururajan, M. et al., Cutting edge: constitutive B cell receptor signaling is critical for basal cell growth of B lymphoma, The Journal of Immunology, 176:5715-5719 (2006).
Hainsworth, J., et al. Rituximab monoclonal antibody as initial therapy for patients with low-grade non-Hodgkin lymphoma, Blood, 95:3052-3056 (2000).
Hallek, M. et al. Guidelines for the diagnosis and treatment of chronic lymphocytic leukemia: a report from the International Workshop on Chronic Lymphocytic Leukemia updating the National Cancer Institute—Working Group 1996 guidelines, Blood, 111:5446-5456 (2008).
Hallek, M. et al., Addition of rituximab to fludarabine and cyclophosphamide in patients with chronic lymphocytic leukaemia: a randomized, open-label, phase 3 trial, Lancet, 376:1164-1174 (2010).
Hamblin, T. et al., Unmutated Ig VH genes are associated with a more aggressive form of chronic lymphocytic leukemia, Blood, 94(6):1848-1854 (1999).
Hauser, S. et al., B-cell depletion with rituximab in relapsing remitting multiple sclerosis, The New England Journal of Medicine, 358(7):676-688 (2008).
Hidalgo, M. et al., Phase I and Pharmacologic Study of OSI-774, an Epidermal Growth Factor Receptor Tyrosine Kinase Inhibitor, in Patients With Advanced Solid Malignancies, Journal of Clinical Oncology, 19:3267-3279 (2001).
Horning, Sandra J., Natural history of and therapy for the indolent non-Hodgkin's lymphomas, Seminars in Oncology, 20(5):75-88 (1993).
Hunter, Z. et al., IgA and IgG hypogammaglobulinemia in Waldenström's macroglobulinemia, Haematologica, 95(3):470-475 (2010).
Hur, W. et al., Clinical stage EGFR inhibitors irreversibly alkylate Bmx kinase, Bioorg. Med. Chem. Lett. 18:5916-5919 (2008).
International Search Report for PCT/US09/48784 dated Nov. 16, 2009.
International Search Report for PCT/US10/31714 dated Aug. 13, 2010.
International Search Report for PCT/US10/62432 dated May 26, 2011.
International Search Report for PCT/US11/46926, 2 pages (Dec. 22, 2011).
International Search Report for PCT/US11/58610, 4 pages (Mar. 27, 2012).
International Search Report for PCT/US11/58616, 3 pages (Mar. 27, 2012).
International Search Report for PCT/US11/59726, 3 pages (Mar. 20, 2012).
International Search Report for PCT/US12/62133, 2 pages (Dec. 28, 2012).
Jemal, A. et al., Cancer Statistics, 2010, CA Cancer Journal for Clinicians, 60:277-300 (2010).

(56) References Cited

OTHER PUBLICATIONS

Jin, H. et al., Identification of Btk mutations in 20 unrelated patients with X-linked agammaglobulinemia (XLA), Human Molecular Genetics, 4(4):693-700 (1995).
Kersseboom, R. et al., Constitutive activation of Bruton's tyrosine kinase induces the formation of autoreactive IgM plasma cells, European Journal of Immunology, 40:2643-2654 (2010).
Kimby, E. et al., Update on recommendations for assessing response from the Third International Workshop on Waldenström's Macroglobulinemia, Clinical Lymphoma & Myeloma, 6(5):380-383 (2006).
Kirken, R., Targeting Jak3 for immune suppression and allograft acceptance, Transplant. Proc. 33 :3268-3270 (2001).
Kumar, A., et al, Structure and Clinical Relevance of the Epidermal Growth Factor Receptor in Human Cancer, Journal of Clinical Oncology 26(10):1742-1751 (2008).
Kwak, E. et al., Irreversible inhibitors of the EGF receptor may circumvent acquired resistance to gefitinib, Proc. Natl. Acad. Sci. USA 102:7665-7670 (2005).
Kyle, R. et al., Prognostic Markers and Criteria to Initiate Therapy in Waldenstrom's Macroglobulinemia: Consensus Panel Recommendations From the Second International Workshop on Waldenstrom's Macroglobulinemia, Seminars in Oncology, 30:116-120 (2003).
Kyriakou, H., on behalf of the Lymphoma Working Party of the European Group for Blood and Bone Marrow Transplantation—Hematopoietic stem cell transplantation for Waldenström's macroglobulinemia, Proceedings of the $5^{th}$ International Workshop on Waldenstrom's macroglobulinemia, Stockholm, Sweden, Abstract 146 (2008).
Küppers Ralf, Mechanisms of B cell lymphoma pathogenesis, Nature Reviews Cancer, 5:251-262 (2005).
Küppers, Ralf, Somatic hypermutation and B cell receptor selection in normal and transformed human B cells, Annals of the New York Academy of Sciences, 987:173-179 (2003).
Lajeunesse, D. et al., A systematic screen for dominant second-site modifiers of Merlin/NF2 phenotypes reveals an interaction with blistered/DSRF and scribbler, Genetics 158:667-79 (2001).
Lanasa, M., Novel insights into the biology of CLL, Hematology (American Society of Hematology), 70-76 (2010).
Lanham, S. et al., Differential signaling via surface IgM is associated with VH gene mutational status and CD38 expression in chronic lymphocytic leukemia, Blood, 101:1087-1093 (2003).
Li, D. et al., BIBW2992, an irreversible EGFR/HER2 inhibitor highly effective in preclinical lung cancer models, Oncogene 27:4702-4711 (2008).
Lin, N. and Winer, E., New targets for therapy in breast cancer: Small molecule tyrosine kinase inhibitors, Breast Cancer Res 6:204-210 (2004).
Maas, A. and Henriks, R., Role of Bruton's tyrosine kinase in B cell development, Development Immunology, 8(3-4):171-181 (2001).
Malaviya, R. et al., Targeting Janus Kinase 3 in Mast Cells Prevents Immediate Hypersensitivity Reactions and Anaphylaxis, J. Biol. Chem. 274 :27028-27038 (1999).
Mattsson, P. et al., X-linked agammaglobulinemia (XLA): a genetic tyrosine kinase (Btk) disease, Bioessays, 18:825-834 (1996).
McClatchey, A. and Giovannini, M., Membrane organization and tumorigenesis—the NF2 tumor suppressor, Merlin, Genes Dev 19:2265-77 (2005).
McLaughlin, P. et al., Rituximab chimeric anti-CD20 monoclonal antibody therapy for relapsed indolent lymphoma; half of patients respond to a four-dose treatment program, Journal of Clinical Oncology, 16:2825-2833 (1998).
Minkovsky, N. and Berezov, A., BIBW-2992, a dual receptor tyrosine kinase inhibitor for the treatment of solid tumors, Curr Opin Invest Drugs 9:1336-1346 (2008).
Mohamed, A. et al., Bruton's tyrosine kinase (Btk): function, regulation, and transformation with special emphasis on the PH domain, Immunological Reviews, 228:58-73 (2009).
Monroe, John G., Ligand-independent tonic signaling in B cell receptor function, Current Opinion in Immunology, 16:288-295 (2004).
Morel, P. et al., International prognostic scoring system for Waldenström macroglobulinemia, Blood, 113:4163-4170 (2009).
Owen, R. et al., Clincopathological definition of Waldenstrom's macroglobulinemia: consensus panel recommendations from the Second International Workshop on Waldenstrom's Macroglobulinemia, Seminars in Oncology, 30(2):110-115 (2003).
Pelton, P. et al., Ruffling membrane, stress fiber, cell spreading and proliferation abnormalities in human Schwann cells, Oncogene 17:2195-2209 (1998).
Pfreundschuh, M. et al., CHOP-like chemotherapy plus rituximab versus CHOP-like chemotherapy alone in young patients with goodprognosis diffuse large B cell lymphoma: a randomized controlled trial by the MabThera International Trial (Mint) Group, Lancet Oncology, 7:379-391 (2006).
Philip, T. et al., Autologous bone marrow transplantation as compared with salvage chemotherapy in relapses of chemotherapy-sensitive non-Hodgkin lymphoma, New England Journal of Medicine, 333:1540-1545 (1995).
Podolanczuk, A. et al., Of mice and men: an open-label pilot study for treatment of immune thrombocytopenic purpura by an inhibitor of Syk, Blood, 113:3154-3160 (2009).
Ponader, S. et al., Bruton's tyrosine kinase inhibitor PCI-32765 abrogates BCR- and nurselike cell-derived activation of CLL cells in vitro and in vivo, Blood, 116(21): Abstract 45 (2010).
PubChem CID 44594695. Feb. 1, 2010. [Retrieved from the Internet May 15, 2011: http://pubchem.ncbi.nlm.nih.gov/summary.cgi?cid=44594695&loc=ec_rcs].
Qiu, Yun and Kung Hsing-Jien, Signaling network of the Btk family kinases, Oncogene, 19:5651-5661 (2000).
Rai, K. et al., Clinical staging of chronic lymphocytic leukemia, Blood, 46(2):219-234 (1975).
Rawlings, D. et al., Activation of BTK by a phosphorylation mechanism initiated by SRC family kinases, Science, 271:822-825 (1996).
Rawlings, D. et al., Mutation of unique region of Bruton's tyrosine kinase in immunodeficient XID mice, Science, 261:358-361 (1993).
Readinger, J. et al., Selective Targeting of ITK Blocks Multiple Steps of HIV Replication, Proc. Natl. Acad. Sci. USA 105: 6684-6689 (2008).
Rituxan (Rituximab), Injection for Intravenous Use; pp. 1-35 (2010).
Rosenwald, A. et al., The use of molecular profiling to predict survival after chemotherapy for diffuse large-B cell lymphoma, New England Journal of Medicine, 346(25):1937-1947 (2002).
Rourke, M. et al., Review of clinical trials conducted in Waldenstrom's macroglobulinemia and recommendations for reporting clinical trial responses in these patients, Leukemia and Lymphoma, 51(10):1779-1792 (2010).
Salles, G., Clinical features, prognosis and treatment of follicular lymphoma, Hematology (American Society of Hematology), 216-225 (2007).
Seidel, H. et al., Pharmaceutical intervention in the JAK/STAT signaling pathway, Oncogene 19: 2645-2656 (2000).
Sequist, L., Second-Generation Epidermal Growth Factor Receptor Tyrosine Kinase Inhibitors in Non-Small Cell Lung Cancer, The Oncologist 12(3):325-330 (2007).
Shome, D. et al., Ulcerative keratitis in gastrointestinal stromal tumor patients treated with perifosine, Ophthalmology, 115:483-487 (2008).
Silverman, Gregg J. and Weisman, Stuart, Rituximab therapy and autoimmune disorders: prospects for anti-B cell therapy, Arthritis & Rheumatology, 48(6):1484-1492 (2003).
Singh, J. et al, Structure-based design of a potent, selective, and irreversible inhibitor of the catalytic domain of the erbB receptor subfamily of protein tyrosine kinases, J. Med. Chem. 40:1130-1135 (1997).
Solal-Céligny P. et al., Follicular Lymphoma International Prognostic Index, Blood, 104:1258-1265 (2004).
Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).
Sudbeck, E. et al., Structure-based Design of Specific Inhibitors of Janus Kinase 3 as Apoptosis-inducing Antileukemic Agents, Clin. Cancer Res. 5: 1569-1582 (1999).

(56) References Cited

OTHER PUBLICATIONS

Supplementary European Search Report for EP10844293.0, 8 pages (Jun. 27, 2013).
Treon S. et al., Primary therapy of Waldenström macroglobulinemia with bortezomib, dexamethasone and rituximab: WMCTG clinical trial 05-180, Journal of Clinical Oncology, 27(23):3830-3835 (2009).
Treon, S. et al., Long-term outcomes to fludarabine and rituximab in Waldenström macroglobulinemia, Blood, 113:3673-3678 (2009).
Treon, Steven P., How I treat Waldenström macroglobulinemia, Blood, 114:2375-2385 (2009).
Trieu, V. et al., A specific inhibitor of janus kinase-3 increases survival in a transgenic mouse model of amyotrophic lateral sclerosis, Biochem. Biophys. Res. Commun. 267:22-25 (2000).
Tullo, A. et al., Ocular findings in patients with solid tumours treated with the epidermal growth factor receptor tyrosine kinase inhibitor gefitinib ('Iressa', ZD1839) in Phase I and II clinical trials, Eye, 19: 729-738 (2005).
Varghese, A. et al., Assessment of bone marrow response in Waldenström's macroglobulinemia, Clinical Lymphoma Myeloma, 9(1):53-55 (2009).
Vihinen, M. et al., BTKbase, mutation database for X-linked agammaglobulinemia (XLA), Nucleic Acids Research, 25(1):166-171 (1997).
Vijay A. and Gertz M., Waldenström macroglobulinemia, Blood, 109:5096-5103 (2007).
Wicker L.S. and Scher, I., X-linked immune deficiency (xid) of CBA/N mice, Current Topics in Microbiology and Immunology, 124:87-101 (1986).
Wierda, W. et al., Ofatumumab as single-agent CD20 immunotherapy in fludarabine-refractory chronic lymphocytic leukemia, Journal of Clinical Oncology, 28(10):1749-1755 (2010).
Wong, K. et al, A phase I study with neratinib (HKI-272), an irreversible pan Erb B receptor tyrosine kinase inhibitor, in patients with solid tumors, Clin. Cancer Res. 15(7):2552-2558 (2009).
Written Opinion for PCT/US09/48784, 9 pages (Nov. 16, 2009).
Written Opinion for PCT/US10/31714 dated Aug. 13, 2010.
Written Opinion for PCT/US10/62432 dated May 26, 2011.
Written Opinion for PCT/US11/46926, 9 pages (Dec. 22, 2011).
Written Opinion for PCT/US11/58610, 8 pages (Mar. 27, 2012).
Written Opinion for PCT/US11/58616, 9 pages (Mar. 27, 2012).
Written Opinion for PCT/US11/59726, 7 pages (Mar. 20, 2012).
Written Opinion for PCT/US12/62133, 11 pages (Dec. 28, 2012).
Yano, S. et al. Distribution and function of EGFR in human tissue and the effect of EGFR tyrosine kinase inhibition, Anticancer Research, 23:3639-3650 (2003).
Zhang, J. et al., Targeting Cancer with Small Molecule Kinase Inhibitors, Nature Rev. Cancer 9:28-39 (2009).
Zhang, Y. et al., Antitumor Activity of Epidermal Growth Factor Receptor-Related Protein Is Mediated by Inactivation of ErbB Receptors and Nuclear Factor-kB in Pancreatic Cancer, Cancer Res 66:1025-1032 (2006).
Zhou, W. et al. Novel mutant-selective EGFR kinase inhibitors against EGFR T790M, Nature, 462(7276): 1070-1074 (2009).
U.S. Appl. No. 14/636,905, filed Mar. 3, 2015, Lee et al.
European Search Report for EP10844293.0, 8 pages (Jun. 27, 2013).
Sjin, R. et al., In vitro and in vivo characterization of irreversible mutant-selective EGFR inhibitors that are wild-type sparing, Molecular Cancer Therapeutics, 13(6):1468-1479 (2014).

* cited by examiner

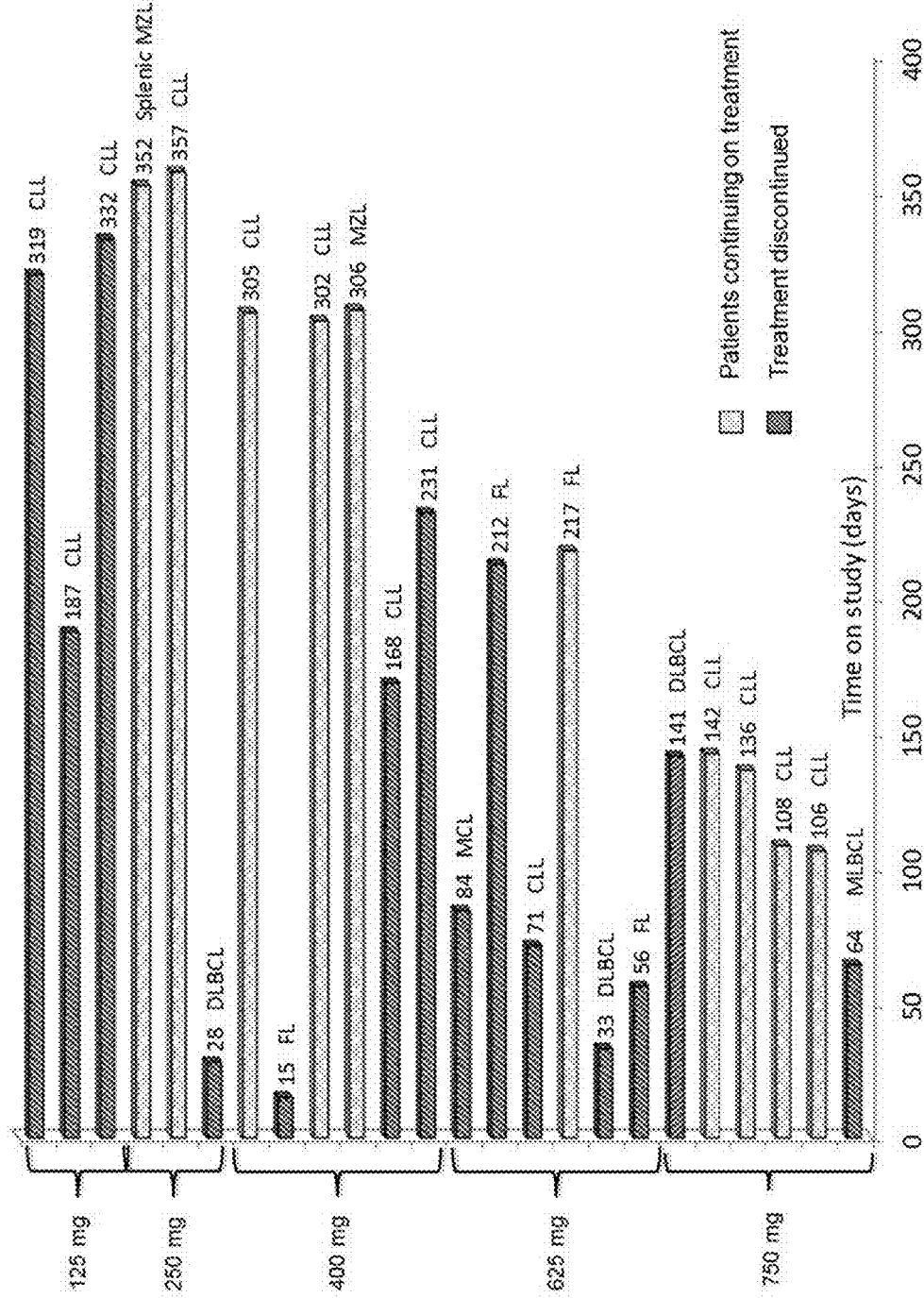

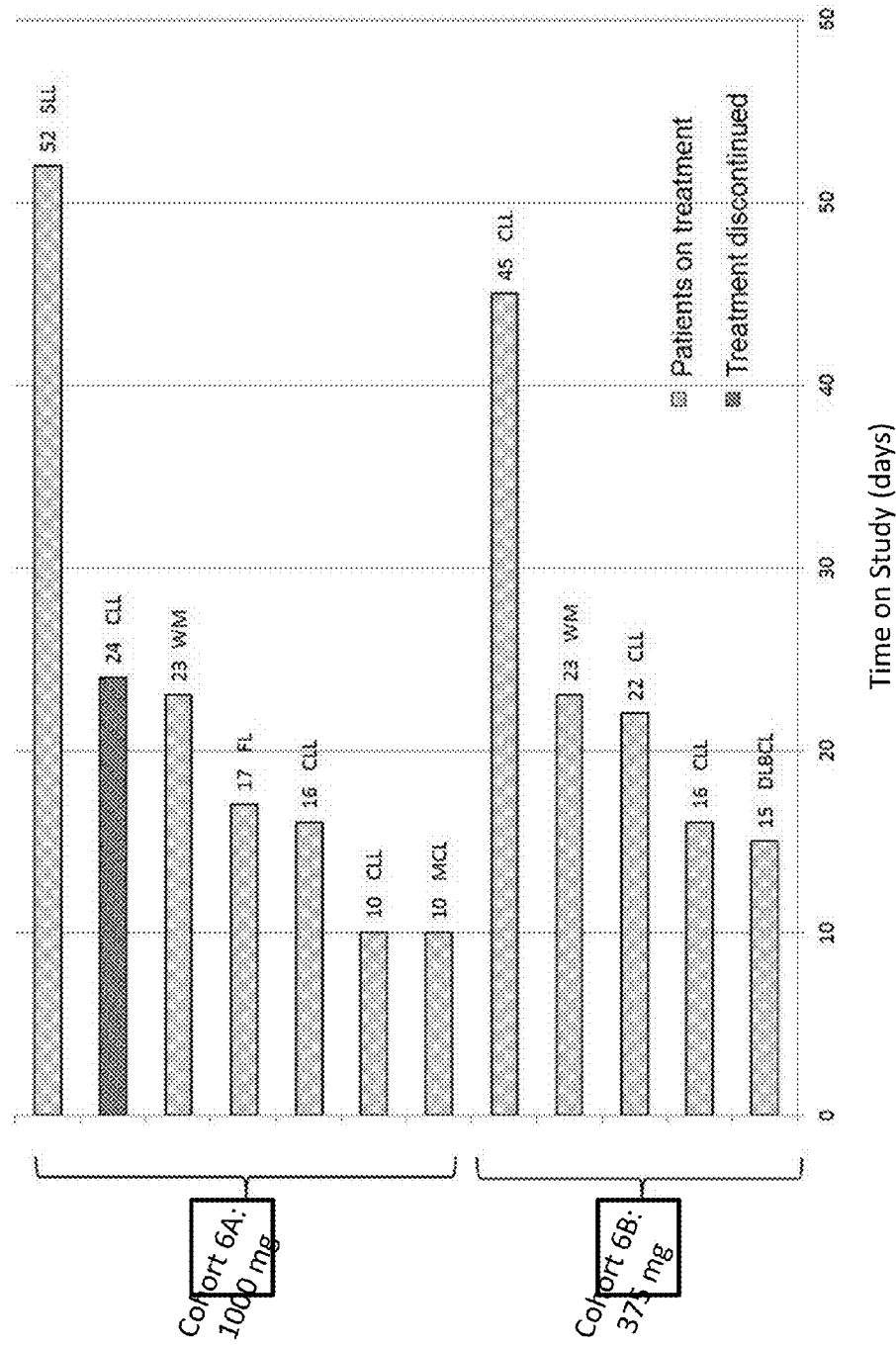
Figure 2. Time on Study - Cohorts 6A and 6B

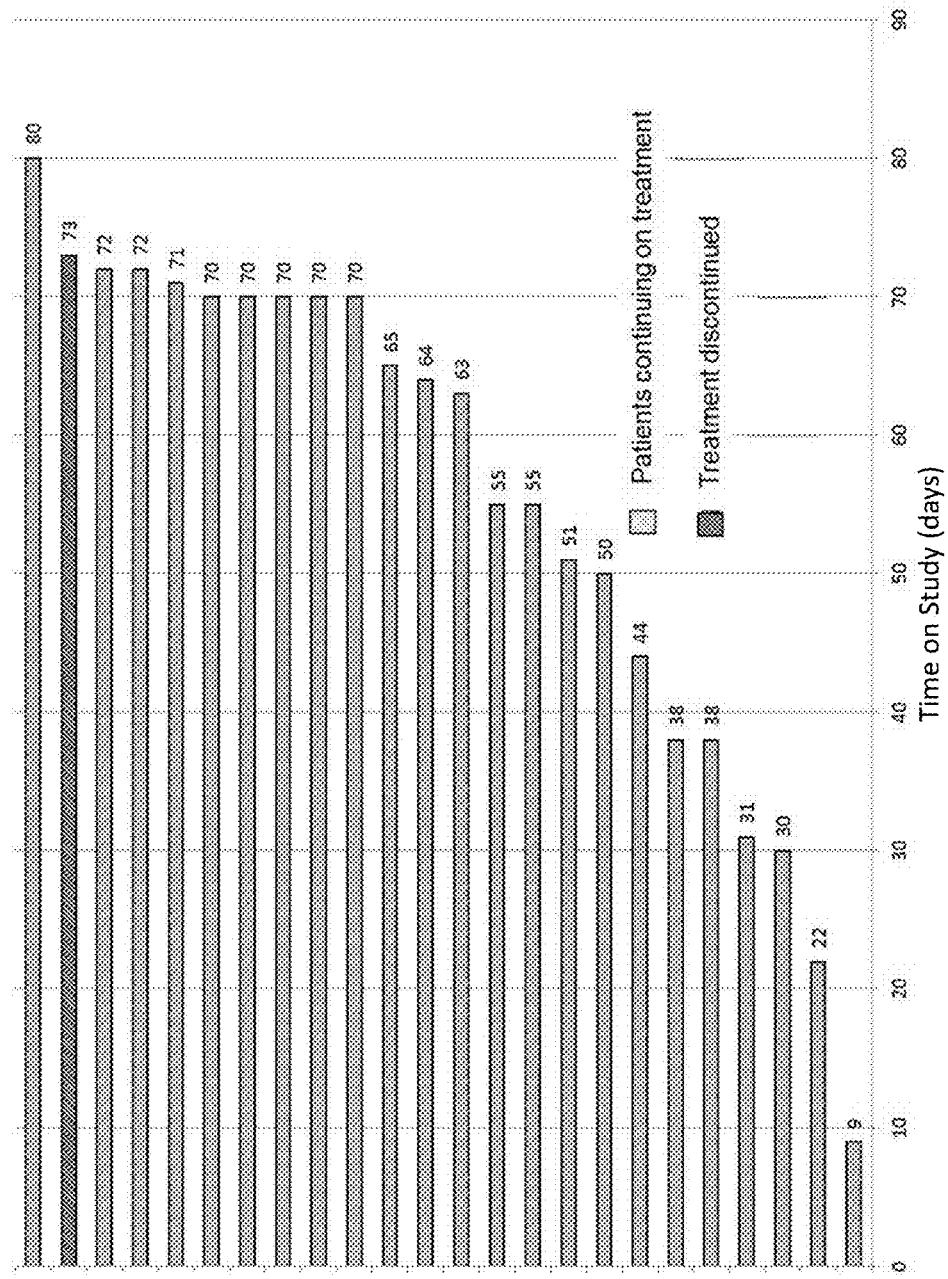
Figure 3. Time on Study: CLL Expansion Cohort C (750 mg QD)

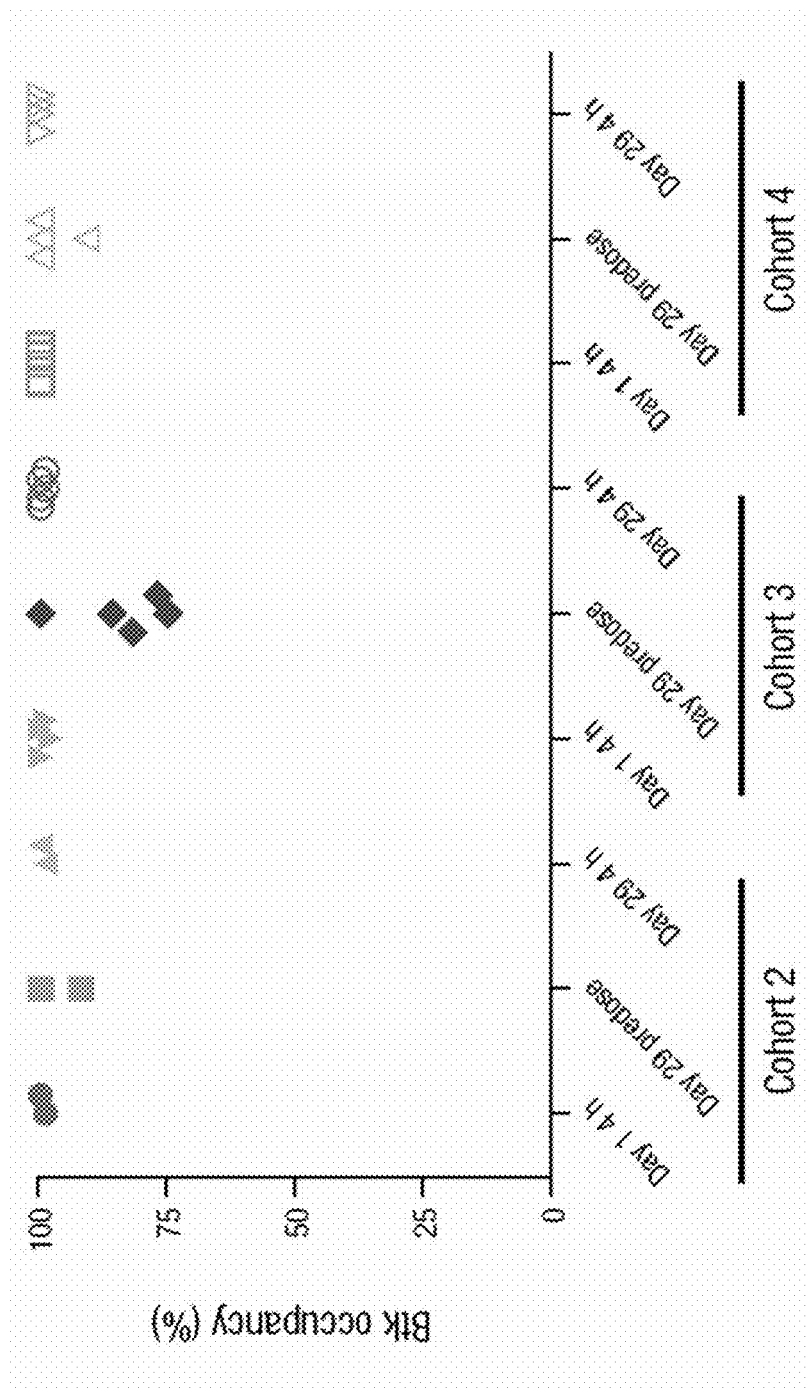

Figure 5. Treatment-Emergent AEs

| AEs, n | All | 125 mg (n = 3) | 250 mg (n = 3) | 400 mg (n = 6) | 625 mg (n = 6) | 750 mg* (n = 3) | Grade 1-2 | Grade 3-4 |
|---|---|---|---|---|---|---|---|---|
| Diarrhea | 15 | 3 | 2 | 4 | 5 | 1 | 15 | 0 |
| Headache | 5 | 2 | 0 | 1 | 2 | 0 | 5 | 0 |
| Thrombocytopenia | 5 | 1 | 0 | 3 | 1 | 0 | 1 | 4 |
| Nausea | 4 | 1 | 1 | 0 | 2 | 0 | 4 | 0 |
| Upper respiratory tract infection | 4 | 2 | 0 | 2 | 0 | 0 | 4 | 0 |
| Fatigue | 4 | 2 | 1 | 1 | 0 | 0 | 4 | 0 |
| Abdominal pain | 3 | 0 | 0 | 0 | 2 | 1 | 3 | 0 |
| Dyspepsia | 3 | 1 | 1 | 0 | 1 | 0 | 3 | 0 |
| Dysgeusia | 3 | 0 | 1 | 0 | 2 | 0 | 3 | 0 |
| Pneumonia | 3 | 1 | 1 | 1 | 0 | 0 | 1 | 2 |
| Neutropenia | 3 | 0 | 1 | 2 | 0 | 0 | 1 | 2 |
| Cough | 3 | 0 | 1 | 2 | 0 | 0 | 3 | 0 |
| Abdominal distension | 2 | 1 | 0 | 0 | 1 | 0 | 2 | 0 |
| Anemia | 2 | 0 | 0 | 1 | 0 | 0 | 2 | 0 |
| Lymph node pain | 2 | 2 | 0 | 0 | 0 | 0 | 2 | 0 |
| Pain in jaw | 2 | 1 | 0 | 1 | 0 | 0 | 2 | 0 |
| Muscle spasm | 2 | 1 | 0 | 1 | 0 | 0 | 2 | 0 |
| Dyspnea | 2 | 0 | 1 | 0 | 1 | 0 | 2 | 0 |
| Influenza-like illness | 2 | 1 | 0 | 1 | 0 | 0 | 2 | 0 |
| Weight loss | 2 | 1 | 0 | 1 | 0 | 0 | 2 | 0 |
| Rash | 2 | 1 | 0 | 0 | 1 | 0 | 2 | 0 |
| Urticaria | 2 | 0 | 0 | 1 | 0 | 0 | 2 | 0 |
| Dehydration | 2 | 0 | 0 | 0 | 2 | 0 | 2 | 0 |
| Urinary retention | 2 | 2 | 0 | 0 | 0 | 0 | 2 | 0 |
| Contusion | 2 | 0 | 0 | 1 | 1 | 0 | 2 | 0 |
| Insomnia | 2 | 0 | 0 | 0 | 2 | 0 | 2 | 0 |
| Eye pain | 2 | 0 | 0 | 1 | 1 | 0 | 2 | 0 |
| Sinusitis | 2 | 1 | 0 | 0 | 1 | 0 | 2 | 0 |

*Patients received 1 cycle of 750 mg before data cutoff.

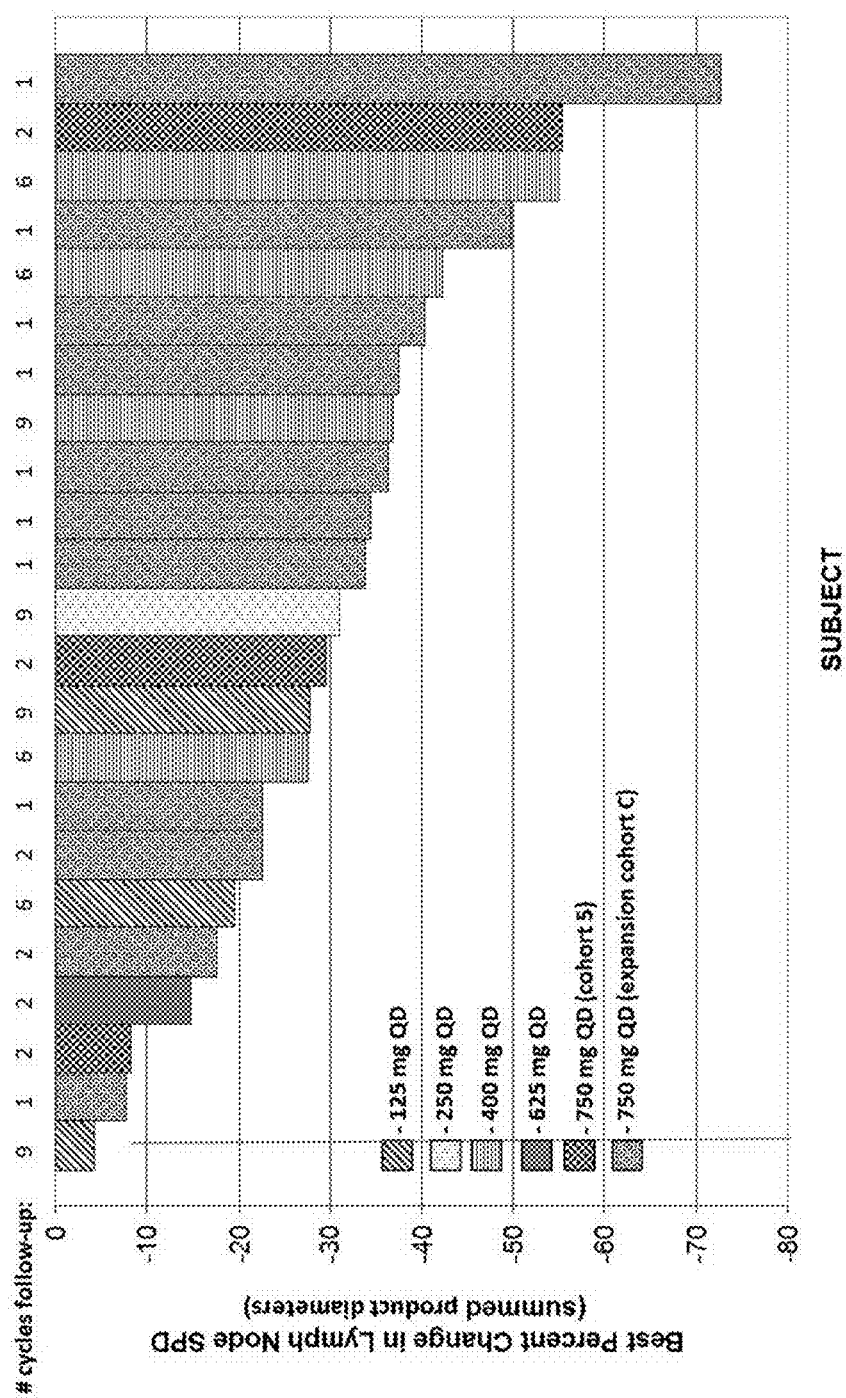

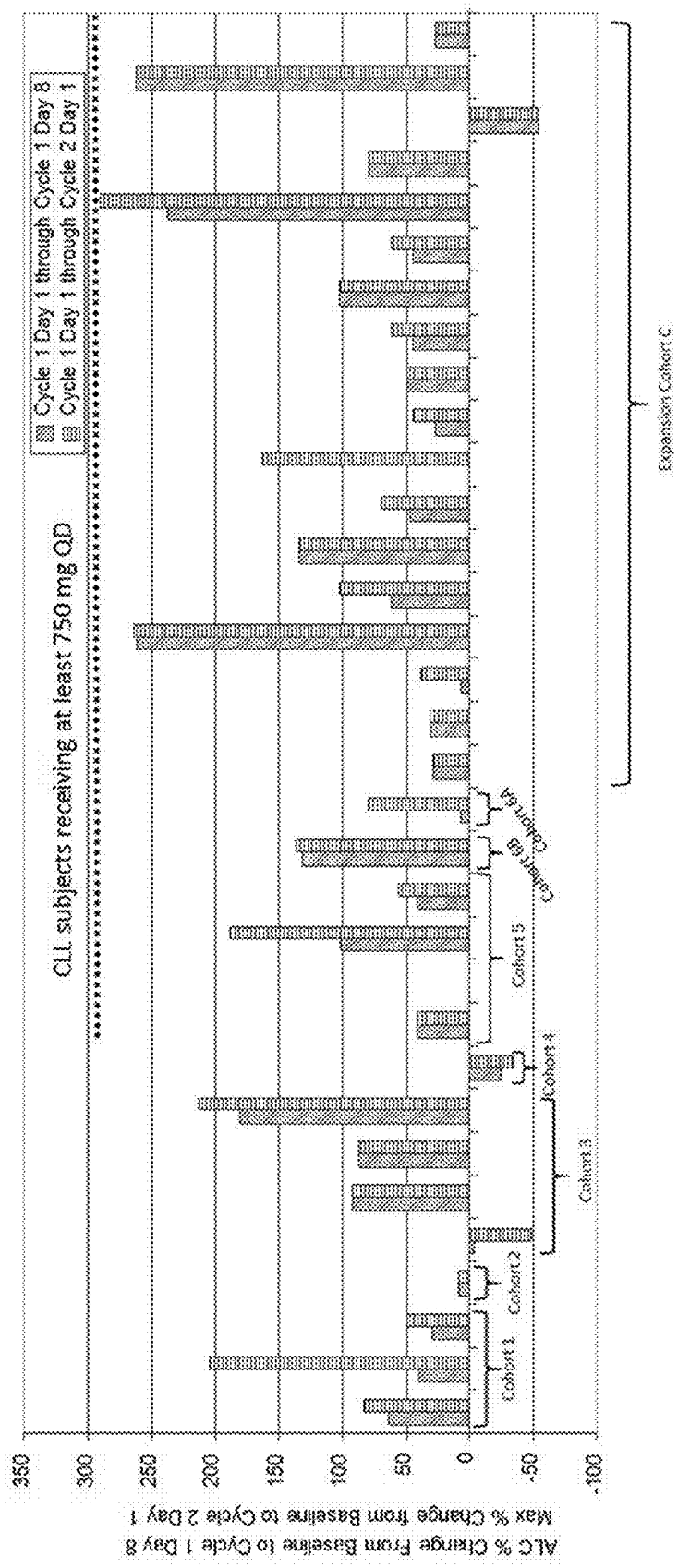
Figure 7. Percent Change in Absolute Lymphocyte Count - All CLL Subjects

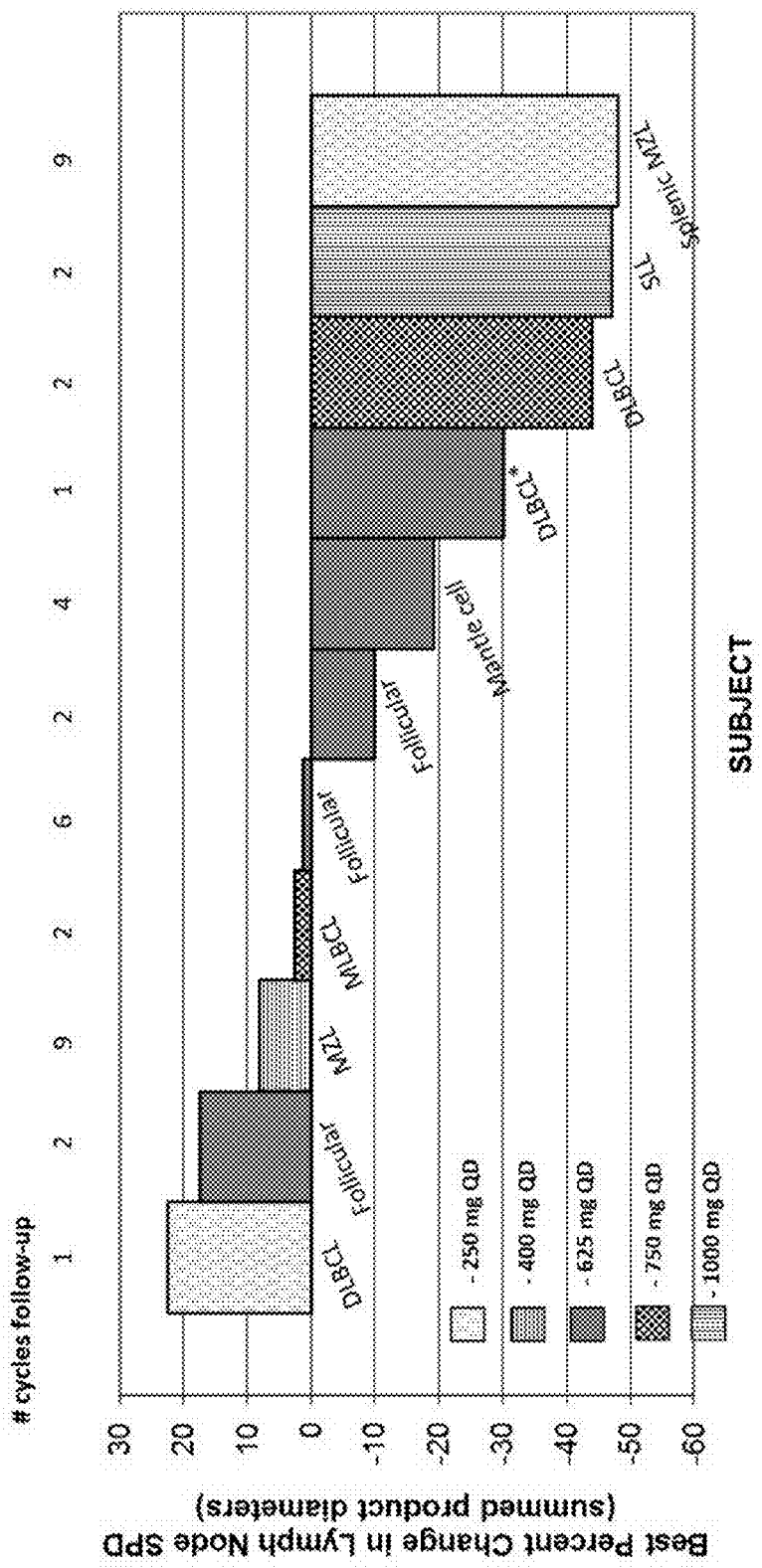

METHODS OF TREATING A BRUTON'S TYROSINE KINASE DISEASE OR DISORDER

CROSS REFERENCE TO RELATED APPLICATIONS

The present application claims priority to U.S. provisional application Ser. Nos. 61/552,936, filed Oct. 28, 2011; 61/569,475, filed Dec. 12, 2011; 61/592,351, filed Jan. 30, 2012; 61/593,056, filed Jan. 31, 2012; 61/604,780, filed Feb. 29, 2012; 61/618,347, filed Mar. 30, 2012; 61/649,450, filed May 21, 2012; and 61/660,319, filed Jun. 15, 2012, the entirety of each of which is hereby incorporated by reference.

FIELD OF THE INVENTION

The present invention provides methods of treating, stabilizing or lessening the severity or progression of a disease or disorder associated with Bruton's Tyrosine Kinase ("BTK").

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor $\alpha$ (TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

The present invention provides methods of treating, stabilizing or lessening the severity or progression of one or more diseases and conditions associated with BTK. In some aspects, the present invention provides methods of treating, stabilizing or lessening the severity or progression of one or more diseases and conditions associated with BTK comprising administering to a patient in need thereof a pharmaceutically acceptable composition comprising N-(3-(5-fluoro-2-(4-(2-methoxyethoxy)phenylamino)pyrimidin-4-ylamino)phenyl)acrylamide (1):

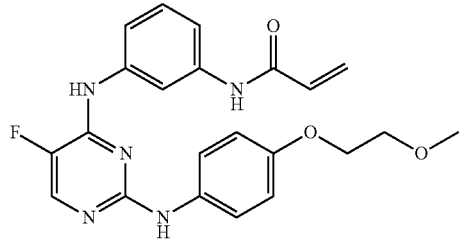

In some embodiments, the present invention provides a method of treating, stabilizing or lessening the severity or progression of one or more diseases and conditions associated with BTK selected from group consisting of B-cell non-Hodgkin's lymphoma, chronic lymphocytic leukemia and Waldenstrom's macroglobulinemia, wherein the method comprises administering to a patient in need thereof a pharmaceutically acceptable composition comprising Compound 1.

In some embodiments, provided methods comprise orally administering to a patient compositions comprising Compound 1. In some embodiments, such compositions are capsule formulations. In general, provided methods comprise administering a composition which comprises Compound 1 and one or more pharmaceutically acceptable excipients, such as, for example, binders, diluents, disintegrants, wetting agents, lubricants and adsorbents.

In some embodiments, the present invention also provides dosing regimens and protocols for the administration of Compound 1 to patients in need thereof.

BRIEF DESCRIPTION OF THE DRAWINGS

FIG. 1 depicts the treatment duration for cohorts 1, 2, 3, 4 and 5 through Sep. 11, 2012. Each subject was administered the respective milligram dose as a continuous daily oral dose. Dotted bars indicate subjects still on treatment as of Sep. 11, 2012. Hashed bars indicate subjects off treatment.

FIG. 2 depicts the treatment duration for cohorts 6A and 6B through Sep. 11, 2012. Each subject was administered the respective milligram dose as an oral dose (1000 mg once daily or 375 mg twice daily). Dotted bars indicate subjects still on treatment as of Sep. 11, 2012.

FIG. 3 depicts the treatment duration for the CLL expansion cohort C through Sep. 11, 2012. Each subject was administered the respective milligram dose as a continuous daily oral dose. Dotted bars indicate subjects still on treatment as of Sep. 11, 2012. Hashed bars indicate subjects off treatment.

FIG. 4 depicts Btk Occupancy with ≥250 mg N-(3-(5-fluoro-2-(4-(2-methoxyethoxy)phenylamino)pyrimidin-4-ylamino)phenyl)acrylamide besylate for cohorts 2, 3 and 4.

FIG. 5 depicts the adverse events reported for cohorts 1, 2, 3, 4 and 5 through May 22, 2012.

FIG. 6 depicts the change in lymph node size in CLL patients during treatment through Sep. 11, 2012.

FIG. 7 depicts the change in absolute lymphocyte count (ALC) in CLL patients during treatment through Sep. 11, 2012.

FIG. 8 depicts the lymph node size percent change in B-NHL patients during treatment through Sep. 11, 2012.

DETAILED DESCRIPTION OF THE INVENTION

Definitions

As used herein, a "disease or disorder associated with BTK" means any disease or other deleterious condition in which BTK, or a mutant thereof, is known or suspected to play a role. Accordingly, another embodiment of the present invention relates to preventing, treating, stabilizing or lessening the severity or progression of one or more diseases in which BTK, or a mutant thereof, is known or suspected to play a role. Specifically, the present invention relates to a method of treating or lessening the severity of a proliferative disorder, wherein said method comprises administering to a patient in need thereof. Compound 1 or a pharmaceutically acceptable composition thereof.

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a "therapeutically effective amount" is at least a minimal amount of a compound, or composition containing a compound, which is sufficient for treating one or more symptoms of a disorder or condition associated with Bruton's tyrosine kinase.

The term "subject", as used herein, means a mammal and includes human and animal subjects, such as domestic animals (e.g., horses, dogs, cats, etc.).

The terms "treat" or "treating," as used herein, refers to partially or completely alleviating, inhibiting, delaying onset of, preventing, ameliorating and/or relieving a disorder or condition, or one or more symptoms of the disorder or condition. As used herein, the terms "treatment," "treat," and "treating" refer to partially or completely alleviating, inhibiting, delaying onset of, preventing, ameliorating and/or relieving a disorder or condition, or one or more symptoms of the disorder or condition, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

The expression "unit dosage form" as used herein refers to a physically discrete unit of inventive formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

Compound 1 is an Irreversible BTK Inhibitor

United States published patent application number US 2010/0029610, published Feb. 4, 2010 ("the '610 publication," the entirety of which is hereby incorporated herein by reference), describes certain 2,4-disubstituted pyrimidine compounds which covalently and irreversibly inhibit activity of one or more protein kinases, including BTK, a member of TEC-kinases. Such compounds include Compound 1, which is designated as compound number I-182 in the '610 publication. The synthesis of Compound 1 is described in detail at Example 20. Compound 1 is active in a variety of assays and therapeutic models demonstrating covalent, irreversible inhibition of BTK (in enzymatic and cellular assays). Notably, Compound 1 was found to inhibit B-cell proliferation and activation. Accordingly, Compound 1 is useful for treating one or more disorders associated with activity of BTK.

The present invention provides methods of treating, stabilizing or lessening the severity or progression of one or more diseases and conditions associated with BTK comprising administering to a patient in need thereof a pharmaceutically acceptable composition comprising Compound 1, wherein the pharmaceutically acceptable composition is an oral dosage form. In some such embodiments, the pharmaceutically acceptable composition is formulated as a capsule. Such methods, dosing regimens and protocols for the administration of pharmaceutically acceptable compositions comprising Compound 1 are described in further detail, below.

I. General Dosing Protocol

As described above, the present invention provides methods of treating, stabilizing or lessening the severity or progression of one or more diseases or conditions associated with BTK, wherein the method comprises administering to a patient in need thereof a pharmaceutically acceptable composition comprising Compound 1. In some embodiments, the present invention provides a method of preventing the progression of a disease or disorder associated with BTK.

In some embodiments, provided methods comprise administering to a patient in need thereof a pharmaceutically acceptable composition comprising from about 5% to about 60% of Compound 1, based upon total weight of the formulation. In some embodiments, provided methods comprise administering to a patient in need thereof a pharmaceutically acceptable composition comprising from about 5% to about 15% or about 7% to about 15% or about 7% to about 10% or about 9% to about 12% of Compound 1, based upon total weight of the composition. In some embodiments, provided methods comprise administering to a patient in need thereof a pharmaceutically acceptable composition comprising from about 25% to about 75% or about 30% to about 60% or about 40% to about 50% or about 40% to about 45% of Compound 1, based upon total weight of the formulation. In certain embodiments, provided methods comprise administering to a patient in need thereof a pharmaceutically acceptable composition comprising from about 6%, about 7%, about 8%, about 9%, about 10%, about 11%, about 12%, about 13%, about 20%, about 30%, about 40%, about 41%, about 42%, about 43%, about 44%, about 45%, about 50%, about 60%, about 70%, or about 75% of Compound 1, based upon total weight of given composition or formulation.

In some embodiments, provided methods comprise administering a pharmaceutically acceptable composition comprising Compound 1 one, two, three, or four times a day. In some embodiments, a pharmaceutically acceptable composition comprising Compound 1 is administered once daily ("QD"). In some embodiments, a pharmaceutically acceptable composition comprising Compound 1 is administered twice daily ("BID"). In some embodiments, a pharmaceutically acceptable composition comprising Compound 1 is administered three times a day ("TID"). In some embodiments, a pharmaceutically acceptable composition comprising Compound 1 is administered four times a day ("QID"). For example, administration of a 375 mg dose of Compound 1 "BID" means that the patient is administered two separate doses of 375 mg in one day.

In some embodiments, provided methods comprise administering a pharmaceutically acceptable composition comprising Compound 1 once a day ("QD"). In some embodiments, a pharmaceutically acceptable composition comprising Compound 1 is administered once daily for a period of 1, 2, 3, 4, 5, 6, 7, 8, 9, 10, 11, 12, 13, 14, 15, 16, 17, 18, 19, 20, 21, 22, 23, 24, 25, 26, 27 or 28 days. In some embodiments, a pharmaceutically acceptable composition comprising Compound 1 is administered once daily for 28 consecutive days ("a 28-day cycle"). In some embodiments, a pharmaceutically acceptable composition comprising Compound 1 is administered once daily for at least one 28-day cycle. In some embodiments, a pharmaceutically acceptable composition comprising Compound 1 is administered once daily for at least two, at least three, at least four, at least five or at least six 28-day cycles. In some embodiments, a pharmaceutically acceptable composition comprising Compound 1 is administered once daily for at least seven, at least eight, at least nine, at least ten, at least eleven or at least twelve 28-day cycles. In some embodiments, a pharmaceutically acceptable composition comprising Compound 1 is administered once daily for at least thirteen, at least fourteen, at least fifteen, at least sixteen, at least seventeen, at least eighteen, at least nineteen or at least twenty 28-day cycles. In some embodiments, a pharmaceutically acceptable composition comprising Compound 1 is administered to a patient for the duration of the patient's life.

In some embodiments, two adjacent 28-day cycles may be separated by a rest period. Such a rest period may be one, two, three, four, five, six, seven or more days during which the patient is not administered a unit dose of Compound 1. In a preferred embodiment, two adjacent 28-day cycles are continuous.

In some embodiments, provided methods comprise administering to a patient in need thereof a pharmaceutically acceptable composition comprising Compound 1, wherein the patient has failed at least one prior therapy.

Unit Dosage Forms

Pharmaceutical compositions for use in the present invention may be prepared as a unit dosage form. A person of ordinary skill will appreciate that the unit dosage forms described herein refer to an amount of Compound 1 as a free base. A person skilled in the art will further appreciate that, when a pharmaceutical composition comprises a salt form of Compound 1, for example a besylate salt form, the amount of the salt form present in the composition is an amount that is equivalent to a unit dose of the free base of Compound 1. For example, a pharmaceutical composition comprising a besylate salt of Compound 1 would contain 34.97 mg of the besylate salt form necessary to deliver an equivalent 25 mg unit dose of the free base of Compound 1.

In some embodiments, provided methods comprise administering to a patient in need thereof a composition comprising a therapeutically effective amount of Compound 1, wherein the therapeutically effective amount is about 125 mg to about 625 mg. In some embodiments, provided methods comprise administering to a patient in need thereof a composition comprising a therapeutically effective amount of Compound 1, wherein the therapeutically effective amount is about 125 mg to about 750 mg. In some embodiments, provided methods comprise administering to a patient in need thereof a composition comprising a therapeutically effective amount of Compound 1, wherein the therapeutically effective amount is about 125 mg to about 1000 mg. In some embodiments, provided methods comprise administering to a patient in need thereof a composition comprising a therapeutically effective amount of Compound 1, wherein the therapeutically effective amount is about 125 mg to about 1250 mg.

In some embodiments, the therapeutically effective amount of Compound 1 is about 125 mg to about 500 mg, or about 125 mg to about 400 mg, or about 125 mg to about 325 mg, or about 125 mg to about 250 mg, or about 250 mg to about 1250 mg, or about 250 mg to about 1000 mg, or about 250 mg to about 750 mg, or about 250 mg to about 625 mg, or about 250 mg to about 500 mg, or about 250 mg to about 400 mg, or about 250 mg to about 325 mg, or about 325 mg to about 1250 mg, or about 325 mg to about 1000 mg, or about 325 mg to about 750 mg, or about 325 mg to about 625 mg, or about 325 mg to about 500 mg, or about 325 mg to about 400 mg, or about 400 mg to about 1250 mg, or about 400 mg to about 1000 mg, or about 400 mg to about 750 mg, or about 400 mg to about 625 mg, or about 400 mg to about 500 mg, or about 500 mg to about 1250 mg, or about 500 mg to about 1000 mg, or about 500 mg to about 750 mg, or about 500 mg to about 625 mg, or about 625 mg to about 1250 mg, or about 625 mg to about 1000 mg, or about 625 mg to about 750 mg.

In some embodiments, the therapeutically effective amount of Compound 1 is about 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1000 mg, 1005 mg, 1010 mg, 1015 mg, 1020 mg, 1025 mg, 1030 mg, 1035 mg, 1040 mg, 1045 mg, 1050 mg, 1055 mg, 1060 mg, 1065 mg, 1070 mg, 1075 mg, 1080 mg, 1085 mg, 1090 mg, 1095 mg, 1100 mg, 1105 mg, 1110 mg, 1115 mg, 1120 mg, 1125 mg, 1130 mg, 1135 mg, 1140 mg, 1145 mg, 1150 mg, 1155 mg, 1160 mg, 1165 mg, 1170 mg, 1175 mg, 1180 mg, 1185 mg, 1190 mg, 1195 mg, 1200 mg, 1205 mg, 1210 mg, 1215 mg, 1220 mg, 1225 mg, 1230 mg, 1235 mg, 1240 mg, 1245 mg or 1250 mg.

In some embodiments, provided methods comprise administering to a patient in need thereof a pharmaceutical composition comprising a unit dose of Compound 1. In some such embodiments, the unit dose is about 25 mg, about 50 mg, about 75 mg, about 100 mg, about 125 mg, about 150 mg, about 175 mg, about 200 mg, about 225 mg or about 250 mg.

II. Uses of Compounds and Pharmaceutically Acceptable Compositions

Compound 1 and compositions described herein are generally useful for the inhibition of protein kinase activity of one or more enzymes. Examples of kinases that are inhibited by Compound 1 and compositions described herein and against which the methods described herein are useful include BTK and other TEC-kinases, including ITK, TEC, BMX and RLK, or a mutant thereof.

Bruton's tyrosine kinase ("BTK"), a member of TEC-kinases, is a key signaling enzyme expressed in most hematopoietic cell types except T lymphocytes. BTK plays an essential role in the B-cell signaling pathway linking cell surface B-cell receptor (BCR) stimulation to downstream intracellular responses.

BTK is a key regulator of B-cell development, activation, signaling, and survival (Kurosaki, Curr. Op. Imm., 2000, 276-281; Schaeffer and Schwartzberg, Curr. Op. Imm. 2000, 282-288). In addition, BTK plays a role in a number of other hematopoietic cell signaling pathways, e.g., Toll like receptor (TLR) and cytokine receptor-mediated TNF-α production in macrophages, IgE receptor (Fc_epsilon_RI) signaling in mast cells, inhibition of Fas/APO-1 apoptotic signaling in B-lineage lymphoid cells, and collagen-stimulated platelet aggregation. See, e.g., C. A. Jeffries, et al., (2003), Journal of Biological Chemistry 278:26258-26264; N. J. Horwood, et al., (2003), The Journal of Experimental Medicine 197: 1603-1611; Iwaki et al. (2005), Journal of Biological Chemistry 280(48):40261-40270; Vassilev et al. (1999), Journal of Biological Chemistry 274(3): 1646-1656, and Quek et al. (1998), Current Biology 8(20): 1137-1140.

Patients with mutations in BTK have a profound block in B-cell development, resulting in the almost complete absence of mature B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B-cells and greatly decreased serum levels of IgM and IgG3. BTK deletion in mice has a profound effect on B-cell proliferation induced by anti-IgM, and inhibits immune responses to thymus-independent type II antigens (Ellmeier et al, J Exp Med 192: 1611-1623 (2000)). BTK also plays a crucial role in mast cell activation through the high-affinity IgE receptor (Fc_epsilon_RI). BTK deficient murine mast cells have reduced degranulation and decreased production of proinflammatory cytokines following Fc_epsilon_RI cross-linking (Kawakami et al. Journal of Leukocyte Biology 65: 286-290).

Compound 1 is an inhibitor of BTK and therefore useful for treating one or more disorders associated with activity of BTK. Thus, in some embodiments, the present invention provides a method of treating, stabilizing or lessening the severity or progression of a BTK-mediated disorder comprising the step of administering to a patient in need thereof N-(3-(5-fluoro-2-(4-(2-methoxyethoxy)phenylamino)pyrimidin-4-ylamino)phenyl)acrylamide, or pharmaceutically acceptable compositions thereof.

As used herein, the term "BTK-mediated" disorders or conditions as used herein means any disease or other deleterious condition in which BTK, or a mutant thereof, is known or suspected to play a role. Accordingly, another embodiment of the present invention relates to treating, stabilizing or lessening the severity or progression of one or more diseases in which BTK, or a mutant thereof, is known or suspected to play a role. Specifically, the present invention relates to a method of treating, stabilizing or lessening the severity or progression of a proliferative disorder, wherein said method comprises administering to a patient in need thereof. Compound 1 or a composition according to the present invention.

Non-Hodgkin's lymphomas (NHL), most of which are classified as B-cell in origin, and chronic lymphocytic leukemia (CLL) comprise a substantial proportion of the overall cancer burden in the United States. For NHL, approximately 65,500 new cases and 20,200 deaths were expected in 2010; while for CLL, approximately 15,000 new cases and 4,400 deaths were predicted. NHL accounts for approximately 4% of incident cancer and cancer deaths in the United States.

1. B-Cell Non-Hodgkin'S Lymphomas

The B-cell non-Hodgkin's lymphomas (B-NHL) exhibit variable clinical behavior and are principally classified on the basis of morphologic criteria. Although many specific entities are recognized, the two most prevalent categories comprise diffuse large B-cell lymphomas (DLBCL), approximately 33% of non-Hodgkin's lymphoma, and the follicular B-cell lymphomas, comprising 20-25%. Other clinically relevant categories include mantle cell, marginal zone (including the extranodal marginal zone lymphoma of mucosa-associated lymphoid tissue, [MALT]), primary mediastinal large B-cell, and Burkitt lymphomas.

Diffuse large B-cell lymphoma typically presents as an aggressive neoplasm with median survival of less than 1 year if left untreated. For several decades, multi-agent chemotherapy with cyclophosphamide, doxorubicin, vincristine, and prednisone (CHOP) was the front-line standard treatment. This regimen produced 41% disease-free and 54% overall survival (OS) at 3 years, and was demonstrated to be as effective as more complicated and toxic chemotherapy regimens. Compared to CHOP alone, the current front-line treatment standard of the anti-CD20 monoclonal antibody rituximab administered concurrently with CHOP (R-CHOP) results in superior event-free survival (EFS) and OS in both poor risk older patients (60-80 years of age; 7 year follow-up: EFS 25% (CHOP) vs. 42% (R-CHOP); OS 35% vs. 53%), as well as in good risk younger patients (18-60 years of age; 3 year follow-up: EFS 59% (CHOP) vs. 79% (R-CHOP); OS 84% vs. 93%). A clinical scoring index, the International Prognostic Index (IPI), was developed to stratify patients by prognosis. More recently, gene expression profiling was utilized to distinguish 3 prognostic groups of patients with DLBCL: germinal center B-cell like, activated B-cell like, and a diffuse type 3 group. These 3 molecular subgroups were not strictly related to any specific histologic sub-type of DLBCL, and they predicted survival following anthracycline-based chemotherapy independently of the IPI. Five year OS following anthracycline-based chemotherapy for the germinal center B-cell-like group was 60% compared with 39% for the diffuse type 3 group, and 35% for the activated B-cell-like group.

Despite the success of R-CHOP in treating DLBCL, some patients relapse. Based largely on the PARMA study, the standard treatment approach to fit patients with relapsed disease is to employ salvage chemotherapy and consolidation with autologous stem cell transplant (ASCT). In the PARMA trial, the use of transplantation following salvage chemotherapy versus continued salvage chemotherapy alone resulted in improved 5 year EFS (46% vs. 12%) and OS (53% vs. 32%).

The follicular NHLs are characterized by a relatively indolent clinical course and high response rates to various chemotherapies, immunotherapies, radioimmunotherapies, and radiation therapy. Not all cases require immediate treatment and "watch and wait" remains an option for some. Nonetheless, most patients eventually require treatment for clinical complications of progressively bulky tumor and undergo multiple courses of treatment characterized by variable degrees of remission followed by successive progressions at shorter and shorter intervals. Median OS from diagnosis in the pre-rituximab era was 8-10 years, although various clinical prognostic and molecular classifications have identified subsets with distinctly poorer outcomes, including some with only 4-5 year median survival. Monotherapy with rituximab produced clinically meaningful responses in both front-line and relapsed follicular lymphoma; and in randomized studies comparing combinations of alkylator and/or anthracycline-based chemotherapies alone versus with rituximab, the addition of rituximab resulted in improved median progression-free and short-term (3-4 year follow-up) OS. However, despite the introduction of rituximab and other advances in the management of advanced stage follicular lymphomas, these diseases remain largely incurable for the majority of those afflicted.

Indolent NHL is a slow-growing or low-grade form of NHL. Indolent NHL types have a relatively good prognosis with a median survival as long as 10 years, but they usually are not curable in advanced clinical stages. Early stage indolent NHL (stages I and II) has traditionally been treated with radiation therapy. However, a continuous rate of relapse is usually seen in advanced stages of indolent NHL. Accordingly, there remains a need for improved therapies for the treatment of indolent NHL. The present invention provides a method of treating, stabilizing or lessening the severity or progression of indolent Non-Hodgkin's lymphoma, wherein said method comprises administering to a patient in need thereof. Compound 1 or a pharmaceutically acceptable composition thereof.

A person of ordinary skill will appreciate that diseases characterized as "B-cell lymphoma" exist as a continuum of diseases or disorders. While the continuum of B-cell lymphomas is sometimes discussed in terms of "aggressive" B-cell lymphomas or "indolent" B-cell lymphomas, a person of ordinary skill will appreciate that a B-cell lymphoma characterized as indolent may progress and become an aggressive B-cell lymphoma. Conversely, an aggressive form of B-cell lymphoma may be downgraded to an indolent or stable form of B-cell lymphoma. Reference is made to indolent and aggressive B-cell lymphomas as generally understood by a person skilled in the art with the recognition that such characterizations are inherently dynamic and depend on the particular circumstances of the individual.

In some embodiments, the B-cell lymphoma is a B-cell non-Hodgkin's lymphoma selected from diffuse large B-cell lymphoma, Burkitt's lymphoma/leukemia, mantle cell lymphoma, mediastinal (thymic) large B-cell lymphoma, follicular lymphoma, marginal zone lymphoma (including extranodal marginal zone B-cell lymphoma and nodal marginal zone B-cell lymphoma), lymphoplasmacytic lymphoma/Waldenstrom macroglobulinemia. In some embodiments, the B-cell lymphoma is chronic lymphocytic leukemia/small lymphocytic lymphoma (CLL/SLL). In some embodiments, the B-cell lymphoma is Waldenstrom macroglobulinemia.

Aggressive B-cell non-Hodgkin's lymphomas include diffuse large B-cell lymphoma (DLBCL), Burkitt's lymphoma/leukemia, mantle cell lymphoma and mediastinal lymphoma.

Indolent or slow-growing B-cell non-Hodgkin's lymphomas include follicular lymphoma, marginal zone lymphoma and lymphoblastic lymphoma/Waldenstrom macroglobulinemia.

2. Chronic Lymphocytic Leukemia

The B-cell disorders chronic lymphocytic leukemia/small lymphocytic lymphoma (CLL/SLL) represent 2 ends of a spectrum of the same disease process differing in the degree of blood/marrow involvement (CLL) versus lymph node involvement (SLL). Chronic lymphocytic leukemia is the most common leukemia in the U.S. and is typically characterized immunophenotypically as CD5+, CD23+, CD10−, CD19+, CD20 dim, sIg dim, and cyclin D1− (the latter point a distinguishing feature from mantle cell lymphoma). Chronic lymphocytic leukemia must also be distinguished from monoclonal B lymphocytosis (absolute monoclonal B-cell count <5000/μL and absence of adenopathy or other clinical features of lymphoproliferative disorder). The understanding of CLL/SLL biology and prognostic factors, and advances in formulating a risk-stratified approach to treatment of CLL/SLL have been recently reviewed by Lanasa, Furman, and the National Comprehensive Cancer Network NHL panel.

Allogeneic stem cell transplant is the only potentially curative treatment for CLL, but 70% of affected patients are ≥65 years of age at the time of diagnosis; have co-morbid conditions limiting eligibility for such therapy; and may exhibit a prolonged natural history with or without specific treatment. The actual prognosis of CLL is variable and dependent principally on clinical stage and certain genetic and molecular features. Both the Rai and Binet clinical staging systems are able to distinguish patient prognostic groups with median OSs ranging from 19 months in the most advanced stage (thrombocytopenia) to >150 months in the earliest stage (blood and marrow lymphocytosis without adenopathy, organomegaly, or defined anemia/thrombocytopenia). Classification by the presence or absence of immunoglobulin heavy gene somatic mutation (IgVH) and by interphase fluorescent in situ hybridization (iFISH) analysis for probed-for acquired chromosomal abnormalities adds additional prognostic discrimination to clinical staging, with unmutated IgVH and del(11q) and del(17p) cytogenetics predicting poorer outcome.

The CLL treatment algorithm is complex and requires first the decision to treat (e.g., presence of symptoms such as fatigue or night sweats; bulky adenopathy/organomegaly; progressive anemia/thrombocytopenia); and second, choice of the treatment regimen, usually involving one or more: purine nucleosides (fludarabine), alkylating agents (cyclophosphamide, chlorambucil, bendamustine), corticosteroids, anti-CD20 monoclonal antibodies (rituximab/ofatumumab), or anti-CD52 monoclonal antibodies (alemtuzumab). The choice of specific therapies depends on the patient's age, disease pattern (eg, primarily nodal versus non-nodal), anticipated drug tolerance and contraindications, and presence or absence of adverse prognostic features such as del(11q) or del(17p). Despite numerous therapies to choose from, treatment options are eventually limited by drug toxicities and resistance, and patients who do not succumb to other maladies endure progressive complications relating to cytopenias, the effects of lymphadenopathy and organomegaly, systemic symptoms, and infectious complications. Given the often elderly character of the patient population, an orally available, well tolerated treatment that exploits a novel weakness of CLL would be welcome.

3. Waldenstrom's Macroglobulinemia

Waldenstrom's Macroglobulinemia (WM) is a malignant B-cell lymphoplasmoproliferative disorder characterized by production of monoclonal pentameric Immunoglobulin M (IgM). Approximately 1000-1500 new cases occur annually in the United States, with an excess in white males. Clinical symptoms relate to tumor infiltration (anemia, thrombocytopenia secondary to marrow infiltration; lymphadenopathy and organomegaly); serum hyperviscosity from the monoclonal IgM excess (bleeding, ocular, neurologic, and cardiovascular symptoms); deposition of IgM in tissues (glomeruli—proteinuria, intestine—diarrhea, skin—papules/nodules); and autoantibody activity of the IgM (chronic immune hemolytic anemia associated with cold agglutinins, peripheral neuropathies). The characteristic lymphoplasmacytic infiltrate in the bone marrow is most often surface IgM positive (sIgM+), CD19+, CD20+, CD22+, and CD79+; although some cases of WM may express CD5, CD10, or CD23. The differential diagnosis includes CLL and mantle cell lymphoma.

Criteria for the initiation of treatment in WM have been defined by a consensus panel of experts, and several recent reviews have summarized treatment recommendations. Initiation of therapy is not based on the IgM level per se but rather on clinical manifestations such as constitutional symptoms, lymphadenopathy/organomegaly, anemia, thrombocytopenia, manifestations of serum hyperviscosity, etc. Recommended first line therapies include rituximab, alkylators (chlorambucil), nucleoside analogs (fludarabine, cladribine), and various combinations of these agents with rituximab. Combinations of rituximab with cyclophosphamide or nucleoside analogs produce overall response rates of 70-80% and complete responses in 10%. Combinations of rituximab with bortezomib and dexamethasone have demonstrated overall response rates of 96%, including 22% with complete response. Consequently, regimens such as rituximab with bortezomib have been recommended as salvage regimens as well as for first line management for patients in need of immediate disease control, since the median time to response with this regimen was only 1.1 months. Other salvage approaches include recycling previously effective first line regimens, thalidomide with rituximab, alemtuzumab, and autologous stem cell and reduced-intensity conditioning allogeneic stem cell transplant.

Rituximab, particularly when administered as monotherapy to patients with high IgM levels >3 g/L, may be associated with an IgM flare that can lead to symptomatic hyperviscosity and other signs and symptoms. The elevated IgM levels may persist for months and do not necessarily portend treatment failure, as evidenced by concurrent reduction in marrow lymphoplasmacytic infiltrate. Conversely, treatment with bortezomib may be associated with rapid reduction in serum IgM levels without significant reduction in bone marrow lymphoplasmacytic infiltrates, suggesting inhibition of IgM secretion without overt cell killing. Indeed, it has been demonstrated that treatment may induce delayed reductions in serum M protein despite prompt reductions in marrow clonal B-cells; while leaving, however, readily identifiable residual CD138+ monoclonal plasma cells in the marrow, explaining the persistent production of the Mprotein. The discordant response between the serum IgM levels and degree of marrow infiltration observed with rituximab and bortezomib based therapies have resulted in the recommendation that in situations where the serum IgM levels may appear out of clinical context, a bone marrow examination be considered to clarify the underlying disease burden.

Despite therapeutic progress and a variety of available treatment options for WM, therapies are limited by adverse tolerance and eventual resistance. WM generally remains incurable and most patients die of disease. A 1999 review reported median survival of 5 years. Ten years later, in 2009, an International Prognostic Scoring System for Waldenstrom's Macroglobulinemia (ISSWM) was reported which analyzed 587 WM patients meeting consensus panel criteria for treatment and reported median survivals from initiation of treatment in risk classified sub-groups ranging from less than 4 years to 12 years, with an overall median of 7 years. In some embodiments, Compound 1 mitigates and/or is effective in treating the rituximab-induced IgM flare in Waldenstrom's macroglobulinemia.

Rationale for Targeting Btk in B-NHL, CLL, and WM

Mechanisms of B-cell lymphoma pathogenesis have recently been reviewed. Most B-cell lymphomas depend on expression of the B-cell receptor for survival, and antigen activation signaling through the BCR seems to be an important factor for lymphoma pathogenesis. An RNA interference genetic screen revealed that the BCR signaling component Btk is essential for survival of activated B-cell like (ABC) DLBCLs with wild type Caspase Recruitment Domain Family Member 11 (CARD11). Small hairpin RNAs (shRNA) targeting Btk were toxic for ABC cell lines with downstream wild type CARD11 but not for cell lines with mutant CARD11 capable of constitutively signaling through the NF-kB pathway, suggesting that further molecular pathway dissection and clinical correlation may open avenues for kinase inhibition strategies that are personalized to the tumor phenotype.

The importance of BCR signaling in CLL has also been studied, in which it has been reported that half of all CLL retain BCR signaling in vitro and that IgVH is an important determinant of BCR responsiveness. Two groups have reported that mutated and unmutated CLL cells respond differentially to IgM ligation of the BCR, with unmutated, but not mutated, CLL cells responding to BCR stimulation with increased global tyrosine phosphorylation and by up-regulating several genes associated with cell cycle regulation and allowing cell growth and expansion. These data highlight the differential role that BCR signaling plays in CLL physiology depending on IgVH mutational status and may suggest a possible differential responsiveness of CLL to inhibitors of BCR signaling. Other in vitro studies have reported that specific Btk inhibition with the investigational agent PCI-32765 produced substantially more apoptosis and cytotoxicity in CLL cells relative to normal B-cells; as well as inducing apoptosis in the face of anti-apoptotic micro-environmental signals, reduction of secretion of chemokines CCL3 and CCL4, and reduction of chemotaxis towards the chemokines CXCL12 and CXCL13. Detailed studies of the pathophysiologic role of Btk in the origin and/or maintenance of WM have not yet been reported. However, a recent report investigating transgenic mouse models demonstrated that constitutively active Btk expression resulted in selective expansion or survival of B-1 cells that were driven into germinal center independent plasma cell differentiation, as evidenced by increased numbers of IgM+ plasma cells in spleen and bone marrow and significantly elevated serum IgM. Anti-nucleosome autoantibodies and glomerular IgM deposition were also observed. However, one study of sequence analysis in 19 WM patients with hypogammaglobulinemia G and/or A failed to find any novel variants in the promoter, flanking introns, or exons of Btk.

Strategies specifically targeting B-cells, for example the B-cell depleting anti-CD20 monoclonal antibodies rituximab and ofatumumab, have demonstrated clinical efficacy in B-cell lymphoma and CLL. Spleen tyrosine kinase (Syk) is a kinase in the BCR signaling pathway proximal to Btk. Inhibition of Syk with the orally available Syk inhibitor fostamatinib disodium produced clinical responses in DLBCL, CLL, and mantle cell lymphoma. Most tellingly, clinical proof of concept for Btk inhibition has been demonstrated by clinical investigations of the orally available Btk inhibitor PCI-32765, which have reported objective anti-tumor responses in patients with DLBCL; mantle cell, marginal zone/mucosa-associated lymphoid tissue (MALT), and follicular lymphoma; Waldenstrom's macroglobulinemia; and CLL/SLL, with good tolerability.

Thus, based on the critical importance of BCR signaling mediated through Btk for the survival and proliferation of various malignant B-cells; Btk's limited cellular expression in B-cells, macrophages, and monocytes; and demonstrated pre-clinical and early clinical proofs of concept that Btk inhibition produces salutary anti-lymphoma, CLL, and WM effects with acceptable clinical tolerability, targeting Btk with a selective Btk inhibitor is a promising and appropriate therapeutic strategy to investigate further in the clinic.

Compound 1 is a potent, selective, orally administered small molecule inhibitor of Bruton's tyrosine kinase (Btk), a major component of the BCR signaling complex. The expression of Btk is limited primarily to B lymphocytes, mast cells, monocytes, and basophils. Compound 1 inhibits Btk activity by binding with high affinity to the ATP binding site of Btk and forming a covalent bond with the target Btk protein, providing rapid, complete, and prolonged inhibition of Btk activity, both in vitro and in vivo.

Both tonic and activated BCR signaling have been implicated in the growth and survival of distinct subtypes of B-cell lymphomas as well as CLL. Reducing the expression of the Immunoglobulin α (Igα) or Immunoglobulin β (Igβ) subunits of the BCR by siRNA knockdown reduced proliferation of B-cell lymphoma cell lines. Additionally, the mutational status of the BCR in CLL is one of the strongest predictors of disease progression, as aggressive disease typically displays BCR encoded by unmutated immunoglobulin variable heavy chains.

III. Methods of Treating Diseases or Disorders Associated with BTK

In some embodiments, the present invention provides a method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a therapeutically effective amount of a pharmaceutically acceptable composition comprising Compound 1, wherein the pharmaceutically acceptable composition is administered as an oral dosage form. In some such embodiments, the oral dosage form is a capsule.

In some embodiments, the present invention provides a method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a solid oral dosage form comprising a unit dose of Compound 1, wherein the unit dose is about 25 mg, about 50 mg, about 75 mg, about 100 mg, about 125 mg, about 150 mg, about 175 mg, about 200 mg, about 225 mg or about 250 mg.

In some embodiments, the present invention provides a method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a pharmaceutical composition comprising Compound 1, wherein the patient has failed at least one prior therapy. In some embodiments, the present invention provides a method of preventing the progression of a disease or disorder selected from the group consisting of B-cell non-Hodgkin's lymphoma, chronic lymphocytic leukemia and Waldenstrom's macroglobulinemia, the method comprising administering to a patient in need thereof a pharmaceutical composition comprising Compound 1, wherein the patient has failed at least one prior therapy.

In some embodiments, the present invention provides a method of treating, stabilizing or lessening the severity or progression of indolent non-Hodgkin's lymphoma, wherein said method comprises administering to a patient in need thereof. Compound 1 or a pharmaceutically acceptable composition thereof. In some embodiments, the indolent non-Hodgkin's lymphoma is selected from follicular lymphoma, marginal zone lymphoma and lymphoblastic lymphoma/Waldenstrom macroglobulinemia. In some embodiments, the indolent non-Hodgkin's lymphoma is selected from follicular lymphoma and marginal zone lymphoma.

In some embodiments, the present invention provides a method of treating, stabilizing or lessening the severity or progression of aggressive non-Hodgkin's lymphoma, wherein said method comprises administering to a patient in need thereof. Compound 1 or a pharmaceutically acceptable composition thereof. In some embodiments, the aggressive non-Hodgkin's lymphoma is selected from diffuse large B-cell lymphoma (DLBCL), Burkitt's lymphoma/leukemia, mantle cell lymphoma and mediastinal lymphoma.

In some embodiments, the present invention provides a method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a pharmaceutical composition comprising about 125 mg to about 625 mg of Compound 1. In some embodiments, the present invention provides a method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a pharmaceutical composition comprising about 125 mg to about 750 mg of Compound 1. In some embodiments, the present invention provides a method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a pharmaceutical composition comprising about 125 mg to about 1000 mg of Compound 1. In some embodiments, the present invention provides a method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a pharmaceutical composition comprising about 125 mg to about 1250 mg of Compound 1.

In some embodiments, the present invention provides a method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a therapeutically effective amount of Compound 1, wherein the therapeutically effective amount comprises about 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1000 mg, 1005 mg, 1010 mg, 1015 mg, 1020 mg, 1025 mg, 1030 mg, 1035 mg, 1040 mg, 1045 mg, 1050 mg, 1055 mg, 1060 mg, 1065 mg, 1070 mg, 1075 mg, 1080 mg, 1085 mg, 1090 mg, 1095 mg, 1100 mg, 1105 mg, 1110 mg, 1115 mg, 1120 mg, 1125 mg, 1130 mg, 1135 mg, 1140 mg, 1145 mg, 1150 mg, 1155 mg, 1160 mg, 1165 mg, 1170 mg, 1175 mg, 1180 mg, 1185 mg, 1190 mg, 1195 mg, 1200 mg, 1205 mg, 1210 mg, 1215 mg, 1220 mg, 1225 mg, 1230 mg, 1235 mg, 1240 mg, 1245 mg or 1250 mg of Compound 1.

In some embodiments, a therapeutically effective amount of Compound 1 is administered one, two, three, or four times daily. In some embodiments, a therapeutically effective amount of Compound 1 is administered once daily ("QD"). In some embodiments, a therapeutically effective amount of Compound 1 is administered twice daily ("BID"). In some embodiments, a therapeutically effective amount of Compound 1 is administered three times a day ("TID"). In some embodiments, a therapeutically effective amount of Compound 1 is administered four times a day ("QID"). In some embodiments, a therapeutically effective amount of Compound 1 is administered once daily (QD), wherein the therapeutically effective amount is 125 mg, 250 mg, 400 mg, 625 mg, 750 mg, 1000 mg or 1250 mg. In some embodiments, a therapeutically effective amount of Compound 1 is administered twice daily (BID), wherein the therapeutically effective amount is 125 mg, 250 mg, 375 mg or 500 mg. In some embodiments, Compound 1 is administered 375 mg BID. In some embodiments, Compound 1 is administered 500 mg BID.

In some embodiments, a therapeutically effective amount of Compound 1 is administered over a period of 28 consecutive days ("a 28-day cycle"). In some embodiments, a therapeutically effective amount of Compound 1 is administered for two, three, four, five or six 28-day cycles. In some embodiments, a therapeutically effective amount of Compound 1 is administered for seven, eight, nine, ten, eleven, twelve or more 28-day cycles. In some embodiments, a pharmaceutically acceptable composition comprising Compound 1 is administered once daily for at least thirteen, at least fourteen, at least fifteen, at least sixteen, at least seventeen, at least eighteen, at least nineteen or at least twenty 28-day cycles. In some embodiments, a therapeutically effective amount of Compound 1 is administered to a patient for the duration of the patient's life.

In some embodiments, two adjacent 28-day cycles may be separated by a rest period. Such a rest period may be one, two, three, four, five, six, seven or more days during which the patient is not administered a unit dose of Compound 1. In a preferred embodiment, two adjacent 28-day cycles are continuous.

In some embodiments, the therapeutically effective amount of Compound 1 is administered to a patient who has failed at least one prior therapy.

Iv. Formulations Comprising Compound 1

As described above, provided methods comprise administering to a patient in need thereof a pharmaceutically acceptable composition comprising Compound 1, wherein the pharmaceutically acceptable composition is an oral dosage form. In some embodiments, the pharmaceutically acceptable composition is formulated as a capsule.

In certain embodiments, provided methods comprise administering to a patient in need thereof a pharmaceutically acceptable composition which comprises Compound 1, and one or more pharmaceutically acceptable excipients, such as, for example, binders, film coatings, diluents, disintegrants, wetting agents, lubricants and adsorbents, or combinations thereof. One skilled in the art will readily appreciate that the category under which a particular component is listed is not intended to be limiting; in some cases a particular component might appropriately fit in more than one category. Also, as will be appreciated, the same component can sometimes perform different functions, or can perform more than one function, in the context of a particular formulation, for example depending upon the amount of the ingredient and/or the presence of other ingredients and/or active compound(s). In some embodiments, the pharmaceutically acceptable composition is a blended powder.

i. Binders and Diluents

Pharmaceutical compositions for use in the present invention may comprise one or more binders. Binders are used in the formulation of solid oral dosage forms to hold the active pharmaceutical ingredient and inactive ingredients together in a cohesive mix. In some embodiments, pharmaceutical compositions of the present invention comprise about 5% to about 50% (w/w) of one or more binders and/or diluents. In some embodiments, pharmaceutical compositions of the present invention comprise about 20% (w/w) of one or more binders and/or diluents. Suitable binders and/or diluents (also referred to as "fillers") are known in the art. Representative binders and/or diluents include, but are not limited to, starches such as celluloses (low molecular weight HPC (hydroxypropyl cellulose), microcrystalline cellulose (e.g., Avicel), low molecular weight HPMC (hydroxypropyl methylcellulose), low molecular weight carboxymethyl cellulose, ethylcellulose), sugars such as lactose (i.e. lactose monohydrate), sucrose, dextrose, fructose, maltose, glucose, and polyols such as sorbitol, mannitol, lactitol, malitol and xylitol, or a combination thereof. In some embodiments, a provided composition comprises a binder of microcrystalline cellulose and/or lactose monohydrate.

ii. Disintegrants

Pharmaceutical compositions for use in the present invention may further comprise one or more disintegrants. Suitable disintegrants are known in the art and include, but are not limited to, agar, calcium carbonate, sodium carbonate, sodium bicarbonate, cross-linked sodium carboxymethyl cellulose (croscarmellose sodium), sodium carboxymethyl starch (sodium starch glycolate), microcrystalline cellulose, or a combination thereof. In some embodiments, provided formulations comprise from about 1%, to about 25% disintegrant, based upon total weight of the formulation.

iii. Wetting Agents

Wetting agents, also referred to as bioavailability enhancers, are well known in the art and typically facilitate drug release and absorption by enhancing the solubility of poorly-soluble drugs. Representative wetting agents include, but are not limited to, poloxamers, polyoxyethylene ethers, polyoxyethylene fatty acid esters, polyethylene glycol fatty acid esters, polyoxyethylene hydrogenated castor oil, polyoxyethylene alkyl ether, polysorbates, and combinations thereof. In certain embodiments, the wetting agent is a poloxamer. In some such embodiments, the poloxamer is poloxamer 407. In some embodiments, compositions for use in the present invention comprise from about 1% to about 30% by weight of wetting agent, based upon total weight of the blended powder.

iv. Lubricants

Pharmaceutical compositions of the present invention may further comprise one or more lubricants. Lubricants are agents added in small quantities to formulations to improve certain processing characteristics. Lubricants prevent the formulation mixture from sticking to the compression machinery and enhance product flow by reducing interparticulate friction. Representative lubricants include, but are not limited to, magnesium stearate, glyceryl behenate, sodium stearyl fumarate and fatty acids (i.e. palmitic and stearic acids). In certain embodiments, a lubricant is magnesium stearate. In some embodiments, provided formulations comprise from about 0.2% to about 3% lubricant, based upon total weight of given formulation.

v. Adsorbents

Pharmaceutical compositions of the present invention may further comprise one or more adsorbents. Representative adsorbents include, but are not limited to, silicas (i.e. fumed silica), microcrystalline celluloses, starches (i.e. corn starch) and carbonates (i.e. calcium carbonate and magnesium carbonate). In some embodiments, provided formulations comprise from about 0.2% to about 3% adsorbent, based upon total weight of given formulation.

vi. N-(3-(5-fluoro-2-(4-(2-methoxyethoxy)phenylamino)pyrimidin-4-ylamino)phenyl)acrylamide besylate As described above, the present invention provides a method of treating a disease or disorder selected from B-cell non-Hodgkin's lymphoma, chronic lymphocytic leukemia and Waldenstrom's macroglobulinemia, the method comprising administering to a patient in need thereof a pharmaceutically acceptable composition comprising Compound 1. The besylate salt of Compound 1, N-(3-(5-fluoro-2-(4-(2-methoxyethoxy)phenylamino)pyrimidin-4-ylamino)phenyl)acrylamide benzenesulfonic acid salt, has recently been identified and is currently in clinical trials as monotherapy in subjects with relapsed or refractory B-cell non-Hodgkin's lymphoma (B-NHL), chronic lymphocytic leukemia (CLL) and Waldenstrom's macroglobulinemia (WM). Thus, in some embodiments, provided methods comprise administering to a patient in need thereof a besylate salt of Compound 1.

In some embodiments, provided methods comprise administering to a patient in need thereof a pharmaceutically acceptable composition comprising from about 5% to about 60% of the besylate salt of Compound 1, based upon total weight of the formulation. In some embodiments, provided methods comprise administering to a patient in need thereof a pharmaceutically acceptable composition comprising from about 5% to about 15% or about 7% to about 15% or about 7% to about 10% or about 9% to about 12% of the besylate salt of Compound 1, based upon total weight of the composition. In some embodiments, provided methods comprise administering to a patient in need thereof a pharmaceutically acceptable composition comprising from about 25% to about 75% or about 30% to about 60% or about 40% to about 50% or about 40% to about 45% of the besylate salt of Compound 1, based upon total weight of the formulation. In certain embodiments, provided methods comprise administering to a patient in need thereof a pharmaceutically acceptable composition comprising from about 8%, about 9%, about 10%, about 11%, about 12%, about 13%, about 20%, about 30%, about 40%, about 41%, about 42%, about 43%, about 44%, about 45%, about 50%, about 60%, about 70%, or about 75% of the besylate salt of Compound 1, based upon total weight of given composition or formulation.

In some such embodiments, provided methods comprise administering to a patient in need thereof a pharmaceutical composition comprising a unit dose of Compound 1, wherein Compound 1 is in the form of a besylate salt. In some such embodiments, the unit dose is an amount sufficient to provide about 25 mg, about 50 mg, about 75 mg, about 100 mg, about 125 mg, about 150 mg, about 175 mg, about 200 mg, about 225 mg or about 250 mg of the free base of Compound 1. In some embodiments, the pharmaceutical composition comprising the besylate salt of Compound 1 is a solid oral dosage form.

In some embodiments, the present invention provides a method of treating, stabilizing or lessening the severity or progression of indolent non-Hodgkin's lymphoma, wherein said method comprises administering to a patient in need thereof the besylate salt of Compound 1 or a pharmaceutically acceptable composition thereof.

In some embodiments, the present invention provides a method of treating, stabilizing or lessening the severity or progression of aggressive non-Hodgkin's lymphoma, wherein said method comprises administering to a patient in need thereof the besylate salt of Compound 1 or a pharmaceutically acceptable composition thereof.

In some embodiments, the present invention provides a method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a composition comprising the besylate salt of Compound 1 and one or more pharmaceutically acceptable excipients selected from binders, film coatings, diluents, disintegrants, wetting agents, lubricants and adsorbents.

In some embodiments, the present invention provides a method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a pharmaceutical composition comprising the besylate salt of Compound 1, wherein the amount of besylate salt is sufficient to deliver about 125 mg, about 250 mg, about 325 mg, about 375 mg, about 400 mg, about 500 mg, about 625 mg, about 750 mg, about 1000 mg or about 1250 mg of the free base of Compound 1. In some such embodiments, the pharmaceutical composition further comprises one or more pharmaceutically acceptable excipients selected from binders, film coating, diluents, disintegrants, wetting agents, lubricants and adsorbents. In some such embodiments, the pharmaceutical composition comprises one or more pharmaceutically acceptable excipients selected from microcrystalline cellulose, lactose monohydrate, sodium starch, poloxamer 407, fumed silica and magnesium stearate.

V. Process for Preparing Pharmaceutical Compositions

Dry Blend Process:

Milled N-(3-(5-fluoro-2-(4-(2-methoxyethoxy)phenylamino)pyrimidin-4-ylamino)phenyl)acrylamide besylate, milled microcrystalline cellulose, milled sodium starch glycolate, milled lactose monohydrate, milled poloxamer 407, and sieved fumed silica are weighed and mechanically blended. An intragranular portion of sieved magnesium stearate (0.5% or 2.0%, per Table 1, below) is added to the blender and the formulation blended. This blended formulation is then roller compacted, milled, and then blended. The remainder or extragranular portion of the magnesium stearate (0.5% or 1.0%, per Table 1, below) is added and the final formulation is blended. Capsules are either mechanically filled or manually filled via the flood fill method.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

Dose Escalation Study

The active pharmaceutical ingredient (API), N-(3-(5-fluoro-2-(4-(2-methoxyethoxy)phenylamino)pyrimidin-4-ylamino)phenyl)acrylamide besylate, is a chemically synthesized small molecule substituted pyrimidine developed as the benzenesulfonic acid salt and is a white to off-white crystalline powder. N-(3-(5-fluoro-2-(4-(2-methoxyethoxy)phenylamino)pyrimidin-4-ylamino)phenyl)acrylamide besylate is an oral, potent ($IC_{50}$<0.5 nM) and selective small molecule inhibitor of Btk. N-(3-(5-fluoro-2-(4-(2-methoxyethoxy)phenylamino)pyrimidin-4-ylamino)phenyl)acrylamide besylate exhibits solubility of approximately 0.16 mg/mL in water and a maximum aqueous solubility of 0.40 mg/mL at approximately pH 3.0. The solubility of N-(3-(5-fluoro-2-(4-(2-methoxyethoxy)phenylamino)pyrimidin-4-ylamino)phenyl)acrylamide besylate in ethanol is approximately 10 mg/mL. N-(3-(5-fluoro-2-(4-(2-methoxyethoxy)phenylamino)pyrimidin-4-ylamino)phenyl)acrylamide besylate exhibits no environmental instabilities (i.e. heat, acid, base) that require special handling.

The API was formulated into capsules containing the components and quantities listed in Table 1 to obtain the study drug. All capsules listed in Table 1 either were administered or will be administered during the dose escalation and expansion cohort studies.

TABLE 1

Components of N-(3-(5-fluoro-2-(4-(2-methoxyethoxy)phenylamino)pyrimidin-4-ylamino)phenyl)acrylamide besylate capsules

| Component | First Generation Capsules | | Second Generation Capsules | |
|---|---|---|---|---|
| | Amount per 25 mg Capsule | Amount per 125 mg Capsule | Amount per 25 mg Capsule | Amount per 125 mg Capsule |
| Capsule shell | 1, size 0 dark green capsule | 1, size 0 white capsule | 1, size 0 white capsule | 1, size 0 white capsule |
| N-(3-(5-fluoro-2-(4-(2-methoxyethoxy)phenylamino)pyrimidin-4-ylamino)phenyl)acrylamide besylate | 34.97 mg (25 mg free base) | 174.86 mg (125 mg free base) | 34.97 mg (25 mg free base) | 174.30 mg (125 mg free base) |
| Microcrystalline cellulose | 186.03 mg | 105.27 mg | 186.03 mg | 101.68 mg |
| Lactose monohydrate | 32.50 mg | 41.50 mg | 32.50 mg | 41.50 mg |
| Sodium starch glycolate | 32.50 mg | 41.50 mg | 32.50 mg | 41.50 mg |
| Poloxamer 407 | 32.50 mg | 41.50 mg | 32.50 mg | 41.50 mg |
| Fumed silica | 3.25 mg | 4.15 mg | 3.25 mg | 4.15 mg |
| Magnesium stearate | 3.25 mg† | 6.23 mg^ | 3.25 mg† | 10.38 mg‡ |

†0.5% (1.625 mg) intragranular; 0.5% (1.625 mg) extragranular.
^0.5% (2.08 mg) intragranular; 1.0% (4.15 mg) extragranular.
‡2.0% (8.30 mg) intragranular; 0.5% (2.08 mg) extragranular.

Study Design: Cohorts 1-5.

Subjects with relapsed or refractory B-NHL, CLL/SLL, or WM who failed at least one prior treatment regimen and who had an ECOG Performance Status grade of 2 or less and exhibit adequate organ function were enrolled in a series of escalating dose cohorts according to a modified Fibonacci sequence. Dose escalation proceeded by a standard "3+3" methodology up to Cohort 5 (750 mg dose), with three patients enrolled to dose level 1 and treated QD for 28 days. Dose escalation, via enrollment in the next higher dose, was allowed only if none (0) of the first three (3) enrolled subjects, or no more than one (1) of the first six (6) enrolled subjects, experienced dose limiting toxicity ("DLT") during the first 28 days of treatment at the lower dose. Intrapatient dose escalation was allowed.

Six (6) dose levels and two (2) contingent dose levels were defined and outlined in Table 2.

TABLE 2

Study Dosing Schema for Escalating Dose Portion of Study

| COHORT | DOSE LEVEL | FREQUENCY |
|---|---|---|
| 1 Starting Dose | 125 mg | QD x 28 d |
| 2 | 250 mg | QD x 28 d |
| 2.5 (contingent)* | 325 mg | QD x 28 d |
| 3 | 400 mg | QD x 28 d |
| 3.5 (contingent)* | 500 mg | QD x 28 d |
| 4 | 625 mg | QD x 28 d |
| 5 | 750 mg | QD x 28 d |

*During the dose escalation study it was intended to proceed directly from dose level 2 to 3 and from dose level 3 to 4 if dose levels 2 and 3 proved safe and well tolerated. Contingent dose levels 2.5 and 3.5 were defined in the event that either dose level 3 or 4 was found to exceed the maximum tolerated dose ("MTD") (≥2 of 6 subjects experience DLTs).

Enrollment for Cohorts 1-5 was not restricted or contingent on the basis of specific B-NHL/CLL/WM diagnosis. Within each cohort, subjects were treated PO (oral) QD (daily) with N-(3-(5-fluoro-2-(4-(2-methoxyethoxy)phenylamino)pyrimidin-4-ylamino)phenyl)acrylamide besylate monotherapy during an initial 28-day treatment cycle and were assessed for safety, tolerability, DLT, pharmacokinetic ("PK"), and pharmacodynamic ("PD"), and disease response. In certain instances, the physician-investigator may elect to rest a patient during the study, during which time the patient does not receive treatment. For example, the physician-investigator may elect to rest a patient due to occurrence or recurrence of adverse events. For purposes of clarity, a patient who has been rested is still enrolled in the study until the physician-investigator determines that the patient should not continue treatment, at which time such patients are discontinued from further treatment. In this context, treatment duration refers to the time a patient is enrolled in the study, inclusive of all rest periods, until treatment is discontinued.

Study Design: Cohorts 6A/B-7A/B.

Beginning with Cohort 6 (1000 mg), twelve (12) patients were enrolled in each subsequent DL and dose. Four (4) dose levels were defined and outlined in Table 3.

TABLE 3

Expanded Cohorts - Cohorts 6A/B and 7A/B

| COHORT | DOSE LEVEL | FREQUENCY |
|---|---|---|
| 6A* | 1000 mg | QD x 28 d |
| 6B* | 375 mg | BID x 28 d |
| 7A+ | 1250 mg | QD x 28 d |
| 7B+ | 500 mg | BID x 28 d |

*Cohorts 6A and 6B were recruited and initiated in parallel with subject enrollment alternating between the two cohorts. If an expanded cohort(s) is simultaneously active, subject enrollment will also alternate with the expanded cohort(s).
+Cohort 7A will proceed provided Cohort 6A proves safe and well-tolerated. Cohort 7B will proceed provided Cohort 6B proves safe and well-tolerated. If an expanded cohort(s) is simultaneously active, enrollment will also alternate with the expanded cohort(s).

Six (6) subjects diagnosed with CLL and six (6) patients diagnosed with B-NHL were enrolled in each of Cohorts 6A and 6B. Cohorts 6A and 6B were enrolled concurrently, and if meeting the requirements for continued escalation, Cohorts 7A and 7B will be enrolled and evaluated. Within each cohort, subjects were treated PO (oral) either QD (daily) or BID (twice daily), as set forth in Table 3, with N-(3-(5-fluoro-2-(4-(2-methoxyethoxy)phenylamino)pyrimidin-4-ylamino) phenyl)acrylamide besylate monotherapy during an initial 28-day treatment cycle and were assessed for safety, tolerability, and dose limiting toxicity ("DLT"), and for pharmacokinetic ("PK"), pharmacodynamic ("PD"), and disease response.

For all cohorts, dose limiting toxicities (DLTs) were specified adverse events (AEs) that observed within the first 28-day cycle and deemed to be related to treatment. Hematologic DLTs were graded in accordance with the International Workshop Criteria 2008 for patients with CLL and the National Cancer Institute Common Terminology Criteria for AEs v4 for patients with B-NHL or WM. Hematologic DLTs included Grade 4 anemia or thrombocytopenia, Grade 4 neutropenia greater than 5 days despite granulocyte colony-stimulating factor (G-CSF) and Grade 3 or higher febrile neutropenia. Non-hematologic DLTs included Grade 3 or higher non-hematologic AEs, with the exception of nausea, vomiting and diarrhea lasting less than 24 hours following medical therapy, tumor lysis syndrome which did not progress to grade 4 and was resolved in less than 7 days with medical management, and transient, rapidly reversible and asymptomatic grade 3 non-hematologic laboratory anomaly.

Subjects without disease progression and without DLT at the end of the first 28-day cycle of treatment will be eligible to continue receiving N-(3-(5-fluoro-2-(4-(2-methoxyethoxy)phenylamino)pyrimidin-4-ylamino)phenyl)acrylamide besylate as monotherapy for additional 28-day cycles until (i) the patient experiences unacceptable toxicity, (ii) the underlying malignancy progresses, (iii) the patient withdraws consent, or (iv) the treating physician-investigator otherwise determines that the patient should not continue treatment. Subjects with CLL experiencing nodal response with lymphocytosis (which may be related to drug-mediated lymphocyte redistribution) were also eligible for additional treatment. Subjects with WM with increasing serum Immunoglobulin M ("IgM") levels at the end of the first 28-day cycle were also evaluated for lymphadenopathy/organomegaly and marrow infiltration. Investigators were permitted to use judgment in determining whether to continue these subjects into the second 28-day cycle if there was a discordant response between increased IgM and stable or decreased lymphadenopathy/organomegaly and marrow infiltration.

Dose escalation will continue until a DLT is observed. Dose escalation, via enrollment in the next higher dose was allowed only if none (0) of the first three (3) enrolled subjects, or no more than one (1) of the first six (6) enrolled subjects in the preceding dose cohort experienced a DLT during the first 28-day cycle of treatment and observation. One key objective for the dose escalation portion of the study was to identify the maximum tolerated dose (MTD) and Optimal Biological Effect dose (OBE). The OBE was defined as:

a. ≥90% target occupancy in 9 of 12 subjects in either peripheral blood or lymph node biopsy at any dose level; and/or b. no further increase in exposure with increasing doses; and/or c. results in a ≥25% increase in lymphocytosis in 4/6 CLL subjects sub-cohort during cycles 1 through 3.

Results

Summary of Study Results.

Sixty (60) patients with previously treated CLL or B-NHL were enrolled as of Sep. 11, 2012. Thirty-six (36) patients were enrolled in dose escalation cohorts 1-6A/B as follows:

TABLE 4

Number of Patients in Dose Escalation Cohorts

| Cohort | Dose | Number of Enrolled Patients |
|---|---|---|
| 1 | 125 mg QD | 3 |
| 2 | 250 mg QD | 3 |
| 3 | 400 mg QD | 6 |
| 4 | 625 mg QD | 6 |
| 5 | 750 mg QD | 6 |
| 6A | 1000 mg QD | 7 |
| 6B | 375 mg BID | 5 |

Another twenty-four (24) patients were enrolled in the CLL expansion cohort, discussed in greater detail below in Example 2. Nineteen (19) patients were diagnosed with CLL in dose escalation cohorts 1-6A/B. The thirteen CLL patients in cohorts 1-5 exhibited the following chromosomal abnormalities (fluorescent in situ hybridization, FISH): two (2) 17p−, one (1) 11q22−, one (1) 17p−/11q22−/13q−/+12, one (1) 17p−/11q22−/13q−, one (1) 17p−/13q−; one (1) 11q22−/13q−, one (1) 13q−/+12, one (1) +12, three (3) with no identifiable chromosomal abnormalities, and one (1) with unknown chromosomal status. Three (3) of the thirteen had mutated IGHV, eight (8) had unmutated IGHV, and in two (2) the IGHV status was unknown.

Seventeen (17) patients were diagnosed with B-NHL (4 diffuse large B cell lymphoma (DLBCL); 5 follicular (FL); 1 splenic marginal zone (sMZL), 1 marginal zone lymphoma (MZL); 2 mantle cell lymphoma (MCL), 2 Waldenstrom's Macroglobulinemia (WM), 1 mediastinal large B cell lymphoma (MLBCL) and 1 small lymphocytic lymphoma (SLL)).

Twenty-four (24) patients were administered API in one of five cohorts of 125, 250, 400, 625 or 750 mg po QD using a 3+3 design in continuous 28 day cycles until progressive disease (PD) or toxicity. Twelve (12) patients were administered API in one of two cohorts of 1000 mg po QD (7 patients) or 375 mg po BID (5 patients). Of the twelve patients in cohorts 6A and 6B, six patients were diagnosed with CLL and six patients were diagnosed with B-NHL. Key objectives were safety, DLT, MTD, PK and Btk occupancy. Plasma API levels were assessed by LC-MS-MS. Btk occupancy levels were assessed by covalent probe assay in peripheral blood mononuclear cells. To date, twenty-three of thirty-six patients continue on treatment, with a median time of treatment of 77.5 days (range of 9-357 days).

Cohort 1.

Three subjects suffering from CLL were enrolled in the first cohort (125 mg). The one male and two female cohort 1 patients had a median age of 59 (range of 45-64), with a median of 2 prior therapies (range of 2-10). None of the subjects showed DLT or disease progression and treatment was continued. Two of the three patients in cohort 1 (125 mg) were escalated to 250 mg at or near the end of the fourth 28-day cycle. One of the two subjects at the escalated 250 mg dose was further escalated to 625 mg at or near the end of the tenth 28-day cycle. All three patients showed progressive disease after 187 days (6.68 cycles), 319 days (11.4 cycles) and 332 days (11.9 cycles), respectively, and treatment was discontinued.

Cohort 2.

The second cohort consisted of one subject diagnosed with CLL and two subjects diagnosed with B-NHL (one splenic marginal zone lymphoma and one DLBCL). The one male and two female cohort 2 patients had a median age of 69 (range of 67-76), with a median of 5 prior therapies (range of 2-5). Two of the three subjects treated in the second cohort (250 mg) showed no DLT or disease progression, and treatment was continued. The subject diagnosed with DLBCL showed progressive disease after 28 days of treatment and treatment was discontinued. One patient was escalated to 400 mg dose at or near the end of the sixth 28-day cycle. One patient was escalated to 750 mg dose at or near the end of the eleventh 28-day cycle. Both patients are currently in the thirteenth 28-day cycle.

Cohort 3.

The third cohort consisted of four subjects diagnosed with CLL and two subjects diagnosed with B-NHL (one marginal zone lymphoma and one follicular lymphoma). The three male and three female cohort 3 patients had a median age of 69 (range of 51-79), with a median of 2.5 prior therapies (range of 1-5). Three patients, one diagnosed with marginal zone lymphoma (MZL) and two diagnosed with CLL, treated in the third cohort (400 mg) showed no DLT or disease progression and treatment was continued. The patient with marginal zone lymphoma (MZL) was escalated to 625 mg dose at or near the end of the seventh 28-day cycle. The CLL patients continued to show no DLT or disease progression and are currently in the eleventh 28-day cycle of treatment. The subject diagnosed with follicular lymphoma experienced dose limiting toxicity thrombocytopenia (low platelet count; Grade 4) and treatment was discontinued before the completion of the first 28-day cycle. The remaining CLL patients showed progressive disease, one after 168 days (six cycles) and one after 231 days (eight cycles), and treatment was discontinued.

Cohort 4.

The fourth cohort consisted of one subject diagnosed with CLL and five subjects diagnosed with B-NHL (three follicular lymphoma, one mantle cell lymphoma (MCL) and one DLBCL). The three male and three female cohort 4 patients had a median age of 62.5 (range of 52-74), with a median of 1.5 prior therapies (range of 1-6). One patient (follicular lymphoma) showed no DLT or disease progression and continued to treatment for seven, and is currently in the eighth 28-day cycle. Four patients have exhibited progressive disease. The mantle cell lymphoma patient exhibited progressive disease after 105 days (3.75 cycles) and treatment was discontinued. The DLBCL patient exhibited progressive disease after 33 days (1.18 cycles) and treatment was discontinued. The remaining two follicular lymphoma patients exhibited progressive disease after two cycles (56 days) and 7.6 cycles (212 days), respectively, and treatment was discontinued. The CLL patient exhibited neutropenia (adverse event) after completion of three cycles (85 days) and treatment was discontinued.

Cohort 5.

The fifth cohort consisted of four subjects diagnosed with CLL, one subject diagnosed with B-NHL (DLBCL) and one subject diagnosed with mediastinal large B cell lymphoma (MLBCL). The four male and two female cohort 5 patients had a median age of 67 (range of 43-81), with a median of 3 prior therapies (range 2-6). Five patients showed no DLT or disease progression and treatment was continued. Two CLL patients have completed three, and are currently in the fourth 28-day cycle. The two remaining CLL patients have completed four, and are currently in the fifth 28-day cycle. The DLBCL patient completed five 28-day cycles before discontinuing treatment due to an unrelated adverse event. The MLBCL patient exhibited progressive disease after 64 days (2.3 cycles) and treatment was discontinued.

Cohorts 6A and 6B.

The sixth cohort consisted of six subjects with CLL, two subjects with Waldenstrom's Macroglobulinemia (WM), one subject with FL, one subject with SLL, one subject with DLBCL and one subject with MCL. As of Sep. 11, 2012 eleven patients showed no DLT or disease progression and continue to receive N-(3-(5-fluoro-2-(4-(2-methoxyethoxy)phenylamino)pyrimidin-4-ylamino)phenyl)acrylamide besylate as continuous monotherapy. Enrollment in Cohorts 6A and 6B is ongoing.

FIG. 1 depicts the treatment duration for cohorts 1, 2, 3, 4 and 5. FIG. 2 depicts the treatment duration for cohorts 6A and 6B. The dotted bars indicate subjects still on treatment as of Sep. 11, 2012. The hashed bars indicate subjects off treatment. Each subject was administered the respective milligram dose once daily for cohorts 1-5 and 6A or twice daily for cohort 6B.

Btk Occupancy.

The covalent mechanism of action of N-(3-(5-fluoro-2-(4-(2-methoxyethoxy)phenylamino)pyrimidin-4-ylamino)phenyl)acrylamide besylate allowed for development of a covalent probe to detect free, uninhibited Btk in lysates derived from tissue culture, animal tissues, or clinical samples. PBMC lysates isolated from whole blood samples 30 minutes before dosing, 4 hours or 24 hours post-dose were incubated with the biotinylated covalent probe. Uninhibited Btk was captured by the covalent probe and quantitated by ELISA. Normalization to untreated control sample allowed for determination of the % Btk occupancy.

Btk Target Site Occupancy ELISA:

Cell lysates or spleen homogenates were incubated with 1 μM $N^1$-(3-(3-(4-(3-acrylamidophenylamino)-5-methylpyrimidin-2-ylamino)phenoxy)propyl)-$N^5$-(15-oxo-19-((3aS,4S,6aR)-2-oxohexahydro-1H-thieno[3,4-d]imidazol-4-yl)-4,7,10-trioxa-14-azanonadecyl)glutaramide (2) in a PBS, 0.05% Tween-20, 1% BSA solution for 1 h at room temperature. Compound 2 has the following structure:

Standards and samples were transferred to a streptavidin-coated 96-well ELISA plate and mixed while shaking for 1 h at room temperature. The α-Btk antibody (BD 611116, 1:1000 dilution in PBS+0.05% Tween-20+0.5% BSA) was then incubated for 1 h at room temperature. After wash, goat α-mouse-HRP (1:5000 dilution in PBS+0.05% Tween-20+ 0.5% BSA) was added and incubated for 1 h at room temperature. The ELISA was developed with addition of tetramethyl benzidine (TMB) followed by Stop Solution and read at OD 450 nm. The standard curve (11.7-3000 pg/μL) was generated with human full-length recombinant Btk protein and plotted using a 4 parameter curve fit in GenS software. Uninhibited Btk detected from samples was normalized to μg total protein as determined by BCA protein analysis (Pierce Cat. 23225).

FIG. 4 depicts the Btk occupancy for cohorts 2, 3 and 4. Complete target occupancy was achieved 4 hours after N-(3-(5-fluoro-2-(4-(2-methoxyethoxy)phenylamino)pyrimidin-4-ylamino)phenyl)acrylamide besylate dosing at each dose level in all cases. Occupancy from only one of three patients in cohort 1 was evaluable and demonstrated 76% occupancy 4 hours post-dose and 36% occupancy on day 29 pre-dose. These results suggest that dose levels achieving Btk occupancy identified in N-(3-(5-fluoro-2-(4-(2-methoxyethoxy)phenylamino)pyrimidin-4-ylamino)phenyl)acrylamide besylate also deliver complete occupancy with repeated once daily dosing in patients with CLL and B-NHL. Btk occupancy for cohorts 5, 6A and 6B are under evaluation.

Adverse Events.

FIG. 5 depicts the adverse events reported for cohorts 1, 2, 3, 4 and initial cohort 5 through May 22, 2012. Adverse events for expanded cohort 5, as well as cohorts 6A and 6B, are under review.

Subjects in cohort 1 reported incidences of contusion (bruising) (2 patients), diarrhea (3 patients), nausea (1 patient), upper respiratory infection (2 patients), fatigue (2 patients), headache (2 patients), pneumonia (1 patient), thrombocytopenia (1 patient), dyspnea (1 patient), lymph

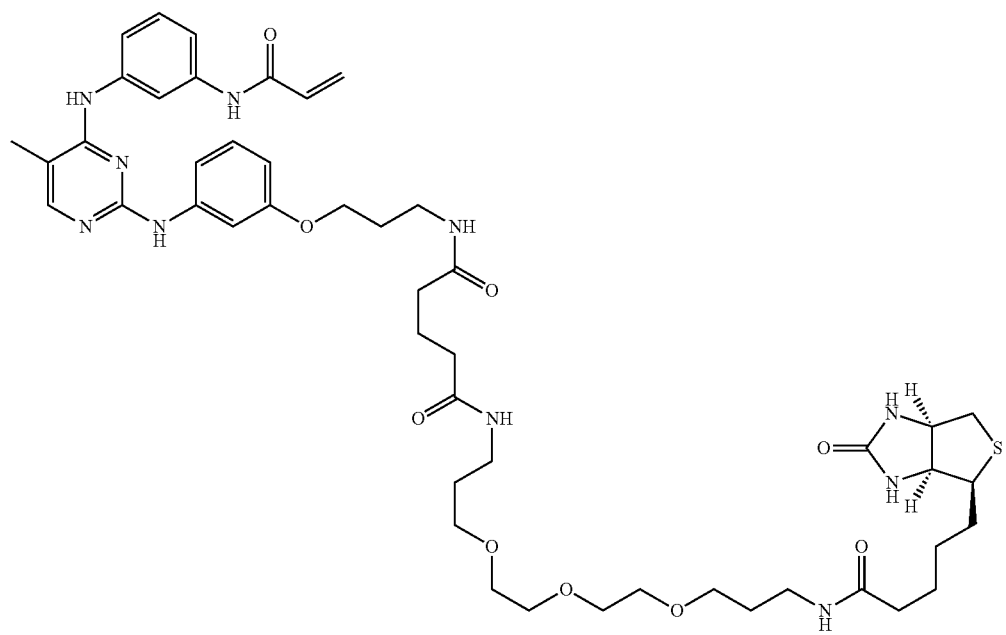

2 node pain (2 patients), dyspepsia (1 patient), abdominal distension (1 patient), jaw pain (1 patient), muscle spasm (1 patient), weight loss (1 patient), rash (1 patient), urticaria (1 patient) and sinusitis (1 patient).

Subjects in cohort 2 reported incidences of decreased diarrhea (2 patients), nausea (1 patient), fatigue (1 patient), pneumonia (1 patient), cough (1 patient), dyspnea (1 patient), dysgeusia (1 patient), neutropenia (1 patient), abdominal distension (1 patient) and weight loss (1 patient).

Subjects in cohort 3 reported incidences of diarrhea (4 patients), upper respiratory infection (2 patients), pneumonia (1 patient), thrombocytopenia (3 patients), neutropenia (2 patients), cough (2 patients), headache (1 patient), fatigue (1 patient), anemia (1 patient), jaw pain (1 patient), muscle spasm (1 patient), influenza-like illness (1 patient), rash (1 patient), urticaria (1 patient), urinary retention (1 patient) and insomnia (1 patient).

Subjects in cohort 4 reported incidences of diarrhea 5 patients), nausea (2 patients), thrombocytopenia (1 patient), headache (2 patients), neutropenia (1 patient), abdominal pain (2 patients), dyspepsia (2 patients), dysgeusia (2 patients), anemia (1 patient), influenza-like illness (1 patient), dehydration (2 patients), urinary retention (1 patient), insomnia (1 patient), eye pain (2 patients) and sinusitis (1 patient).

Subjects in cohort 5 reported incidences of diarrhea (1 patient) and abdominal pain (1 patient).

Adverse events reported were severity Grade 1 and 2 except for decreased ANC (neutropenia), pneumonia and thrombocytopenia. Four (4) patients reported Grade 3-4 thrombocytopenia. Two (2) patients reported Grade 3-4 pneumonia. Three (3) patients reported Grade 3-4 neutropenia.

Besides the DLT reported for the follicular lymphoma patient in cohort 3, no other DLTs have occurred and MTD has not been reached. Serious adverse events not related to the study include disseminated Herpes zoster (1 patient in cohort 1), pneumonia (1 patient in cohort 1), atrial fibrillation (1 patient in cohort 2), hematuria/urinary retention (1 patient in cohort 3), pneumonia/thrombocytopenia/ANC decreased (1 patient in cohort 3) and tonsillar hypertrophy (1 patient in cohort 4).

Most frequent treatment emergent AEs (TEAEs) (defined as an adverse event reported for at least 2 subjects regardless of dose) included grade 1 or 2 transient diarrhea (15/21; 71.4%), grade 1 or 2 headache (5/21; 23.8%), and thrombocytopenia (5/21; 23.8%). The most common Grade 3/4 adverse events included neutropenia (3/21; probably related), pneumonia (2/21; probably related) and thrombocytopenia (4/21; probably related).

Lymph Node Size in CLL Patients.

FIG. 6 depicts the change in lymph node size in CLL patients with available lymph node assessment, twelve (12) of whom are from cohorts 1-5. These patients have experienced some degree of lymph node reduction: 2/12 patients have experienced nodal response (>50% reduction); 6/12 patients have experienced between 25 and 50% reduction over the treatment and follow-up periods indicated in the figure. The doses indicated refer to the patient's starting dose. The numbers at the top of each bar indicate the number of cycles completed for each subject as of the last available lymph node measurement.

Absolute Lymphocyte Count in CLL Patients.

FIG. 7 depicts the change in absolute lymphocyte count (ALC) in CLL patients. As of Sep. 11, 2012, eleven (11) of fifteen (15) CLL patients in cohorts 1-6A/B who had completed at least one 28-day cycle and for whom absolute lymphocyte counts (ALC) were available exhibited early increases (≥25%) in absolute lymphocyte counts (ALC) during the first 28-day cycle, which was consistent with the hypothesis that the API affects CLL lymphocyte trafficking FIG. 7 shows the increase or decrease in ALC from baseline to C1D8 (cycle 1, day 8) as well as the percentage change in ALC from baseline to the maximum observed at any time during cycle 1 up to and including day 29 (cycle 2, day 1 or C2D1). All CLL subjects with follow-up through cycle 1 at all dose levels are shown. Subjects treated with 750 mg or higher are indicated under the dotted line.

Lymph Node Size in NHL Patients.

Six B-NHL patients exhibited decreased lymph node size. FIG. 8 depicts the lymph node size percent change for those B-NHL patients who have had a baseline lymph node measurement and at least one follow-up measurement post-treatment. The doses indicated refer to the patient's starting dose. The numbers at the top of each bar indicate the number of cycles completed for each subject as of the last available lymph node measurement. One patient with FL is not displayed because the patient was withdrawn from the study in the first cycle of treatment for DLT and was not evaluable for response.

Observations.

Across the first five doses, once daily dosing with 125 mg, 250 mg, 400 mg, 625 mg and 750 mg N-(3-(5-fluoro-2-(4-(2-methoxyethoxy)phenylamino)pyrimidin-4-ylamino)phenyl)acrylamide besylate was found to be generally safe and well-tolerated. As of Sep. 11, 2012, twenty-one (21) of thirty-six (36) patients in cohorts 1-6A/B continue on treatment, with a median time of treatment of 77.5 days (range of 9-357 days). PK exposure ($AUC_{last}$) was linear with no accumulation from Day 1 to 15. Full Btk occupancy was achieved with dose levels ≥250 mg QD and PK was predictable with no accumulation. Additional study of 750 mg QD is ongoing. MTD has not yet been reached and cohort expansion is planned.

Example 2

Diagnosis-Specific Expansion Cohorts

After completion of observation for DLTs in Example 1, the accumulated safety, PK, and PD data from Example 1 were evaluated to select a preliminary recommended Phase 2 dose for administration to additional subjects enrolled into an independent and non-randomized diagnosis-specific expansion cohorts in the Diagnosis Specific Expansion Cohorts study.

Cohort A: Relapsed and/or refractory diffuse large B-cell lymphoma (DLBCL);

Cohort B: Relapsed and/or refractory indolent and mantle B-cell lymphomas, Waldenstrom's macroglobulinemia, and other B lymphoproliferative disorders of uncertain malignant potential (at least 10 of the 24 enrollment slots will be reserved for subjects with mantle cell lymphoma); and Cohort C: Relapsed and/or refractory CLL/SLL.

Study Results: Cohort C.

24 subjects were enrolled into the CLL expansion cohort C and were assessed for safety, tolerability, DLT, PK, PD and disease response. Each subject was evaluated prior to enrollment to ensure that minimum hematological criteria were satisfied:

TABLE 5

| Minimum Hematological Criteria | |
| --- | --- |
| | CLL |
| Platelets | ≥30,000/mm³ |
| Absolute Neutrophil Count (ANC) | ≥1,000/mm³ |
| Hemoglobin (Hgb) | ≥8 g/dL |

Within cohort C, 24 subjects were treated 750 mg po QD with N-(3-(5-fluoro-2-(4-(2-methoxyethoxy)phenylamino)pyrimidin-4-ylamino)phenyl)acrylamide besylate as monotherapy during an initial 28-day treatment cycle and were assessed for safety, tolerability, DLT, PK, PD, and disease response.

All subjects enrolled in expansion cohort C were continuously evaluated for DLTs (see DLT definitions below). Twenty-four patients showed no DLT and twenty-three patients showed no disease progression and continue to receive N-(3-(5-fluoro-2-(4-(2-methoxyethoxy)phenylamino)pyrimidin-4-ylamino)phenyl)acrylamide besylate as continuous monotherapy. One patient exhibited progressive disease after 73 days (2.6 cycles) and treatment was discontinued. FIG. 3 depicts the treatment duration of the CLL expansion cohort C through Sep. 11, 2012.

FIG. 6 depicts the change in lymph node size in CLL patients with available lymph node assessment, eleven (11) of whom are from Expansion Cohort C. These patients have experienced some degree of lymph node reduction: 1/11 patients has experienced nodal response (>50% reduction); 6/11 patients have experienced between 25 and 50% reduction over the treatment and follow-up periods indicated in the figure.

As of Sep. 11, 2012, seventeen (17) of eighteen (18) patients enrolled in the CLL Expansion Cohort C who had completed at least one 28-day cycle and for whom absolute lymphocyte counts (ALC) were available exhibited early increases (≥25%) in absolute lymphocyte counts (ALC) during the first 28-day cycle, which was consistent with the hypothesis that the API affects CLL lymphocyte trafficking. The ALC for expansion cohort C are presented in FIG. 7.

A similar protocol will be used for expansion cohorts A and B. In particular, however, if in any specific expansion cohort ≥9 subjects experience DLT, then all future subjects enrolling in that specific expansion cohort and subjects then currently still in Cycle 1 of that specific cohort will be dose reduced by 1 dose level (per Table 2). In the event that 2 or more subjects in any specific expansion cohort experience the same DLT of grade ≥4, then all subjects in that cohort will be reduced by 1 dose level, and the investigators and Sponsor will determine whether to apply the dose reduction to all 3 expansion cohorts. If applicable, this dose reduction will also apply to any subjects from Example 2 who entered the Continuation Phase and were intra-subject dose escalated to the initial preliminary recommended Phase 2 dose.

Example 3

Continuation Phase of Treatment

In both Dose Escalation and Diagnosis-Specific Expansion Cohort studies, subjects who complete the first 28-day cycle of therapy will be evaluated for entry into a Continuation Phase of the study. Subjects will be eligible for continuation if: 1) they demonstrate no evidence of disease progression; 2) in the opinion of the investigator, they are deemed likely to continue to benefit from treatment; and 3) they have not experienced any toxicity requiring discontinuation. Subjects with CLL experiencing nodal response with lymphocytosis will also be eligible for additional treatment. Subjects with WM with increased serum IgM levels at the end of 6 cycles of treatment should also be evaluated for lymphadenopathy/organomegaly and marrow infiltration. Investigators may use judgment in determining whether to continue these subjects into continuation cycles if there is a discordant response between increased IgM and stable or decreased lymphadenopathy/organomegaly and marrow infiltration. During continuation therapy, subjects will continue to receive N-(3-(5-fluoro-2-(4-(2-methoxyethoxy)phenylamino)pyrimidin-4-ylamino)phenyl)acrylamide besylate as monotherapy in 28-day cycles until unacceptable toxicity or the subject or investigator decide to discontinue treatment for any reason.

We claim:

1. A method of treating, stabilizing or lessening the severity or progression of a disease or disorder selected from the group consisting of B-cell non-Hodgkin's lymphoma, chronic lymphocytic leukemia and Waldenstrom's macroglobulinemia, the method comprising administering to a patient in need thereof a composition comprising a therapeutically effective amount of Compound 1:

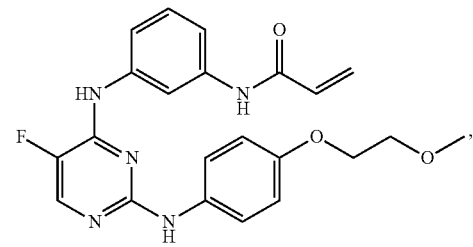

or a pharmaceutically acceptable salt thereof, wherein the therapeutically effective amount is about 750 mg to about 1000 mg.

2. The method of claim 1, wherein the therapeutically effective amount is about 750 mg.

3. The method of claim 1, wherein the therapeutically effective amount is about 1000 mg.

4. The method of claim 2, wherein the therapeutically effective amount is about 375 mg BID.

5. The method of claim 3, wherein the therapeutically effective amount is about 500 mg BID.

6. The method of claim 1, wherein Compound 1 is administered once a day (QD).

7. The method of claim 2, wherein Compound 1 is administered once a day (QD).

8. The method of claim 3, wherein Compound 1 is administered once a day (QD).

9. The method according to claim 1, wherein the B-cell non-Hodgkin's lymphoma is indolent.

10. The method according to claim 9, wherein the B-cell non-Hodgkin's lymphoma is selected from follicular lymphoma and marginal zone lymphoma.

11. The method according to claim 1, wherein the B-cell non-Hodgkin's lymphoma is aggressive.

12. The method according to claim 11, wherein the B-cell non-Hodgkin's lymphoma is selected from diffuse large B-cell lymphoma and mantle cell lymphoma.

13. The method according to claim 1, wherein the composition is formulated as an oral dosage form.

14. The method according to claim 13, wherein the composition is administered once a day.

15. The method according to claim 13, wherein the composition is administered twice a day.

16. The method according to claim 14 or 15, wherein the composition is administered for at least one 28-day cycle.

17. The method according to claim 16, wherein the patient has failed at least one prior therapy.

18. The method according to claim 1, wherein Compound 1 is in the form of a benzenesulfonic acid salt.

19. The method according to claim 18, wherein the composition comprises from about 10% to about 50% N-(3-(5-fluoro-2-(4-(2-methoxyethoxy)phenylamino)pyrimidin-4-ylamino)phenyl)acrylamide besylate.

20. The method according to claim 19, wherein the composition comprises about 10% N-(3-(5-fluoro-2-(4-(2-methoxyethoxy)phenylamino)pyrimidin-4-ylamino)phenyl)acrylamide besylate.

21. The method according to claim 19, wherein the composition comprises about 42% N-(3-(5-fluoro-2-(4-(2-methoxyethoxy)phenylamino)pyrimidin-4-ylamino)phenyl)acrylamide besylate.

22. The method according to claim 1, wherein the composition comprises from about 5% to about 15% by weight of wetting agent.

23. The method according to claim 19, wherein the composition comprises about 10% by weight of wetting agent.

24. The method according to claim 22 or 23, wherein the wetting agent is selected from poloxamer, polyoxyethylene ethers, polyoxyethylene sorbitan fatty acid esters, polyoxyethylene fatty acid esters, polyethylene glycol fatty acid esters, polyoxyethylene hydrogenated castor oil, polyoxyethylene alkyl ether, polysorbates, cetyl alcohol, glycerol fatty acid esters, polyoxymethylene stearate, sodium lauryl sulfate, sorbitan fatty acid esters, sucrose fatty acid esters, benzalkonium chloride, polyethoxylated castor oil, and docusate sodium.

25. The method according to claim 24, wherein the wetting agent is a poloxamer.

26. The method according to claim 25, wherein the poloxamer is poloxamer 407.

* * * * *